US007288249B2

(12) United States Patent
Carter et al.

(10) Patent No.: US 7,288,249 B2
(45) Date of Patent: Oct. 30, 2007

(54) ANTIBODIES FOR CANCER THERAPY AND DIAGNOSIS

(75) Inventors: Paul J. Carter, San Francisco, CA (US); John B. Ridgway, Pacifica, CA (US)

(73) Assignee: Genentech, Inc., South San Francisco, CA (US)

( * ) Notice: Subject to any disclaimer, the term of this patent is extended or adjusted under 35 U.S.C. 154(b) by 639 days.

(21) Appl. No.: 10/447,331

(22) Filed: May 28, 2003

(65) Prior Publication Data

US 2003/0219434 A1 Nov. 27, 2003

Related U.S. Application Data

(62) Division of application No. 09/515,825, filed on Feb. 29, 2000, now abandoned.

(60) Provisional application No. 60/122,262, filed on Mar. 1, 1999.

(51) Int. Cl.
*A61K 39/395* (2006.01)
*C07K 16/00* (2006.01)

(52) U.S. Cl. .............................. 424/130.1; 424/138.1; 424/141.1; 424/155.1; 530/387.1; 530/387.7; 530/288.1; 530/388.8

(58) Field of Classification Search ..................... None
See application file for complete search history.

(56) References Cited

U.S. PATENT DOCUMENTS

| 4,816,567 | A | 3/1989 | Cabilly et al. |
| 5,565,332 | A | 10/1996 | Hoogenboom et al. |
| 5,695,945 | A | 12/1997 | Tsuji |
| 5,733,743 | A | 3/1998 | Johnson et al. |
| 5,763,224 | A | 6/1998 | Caras et al. |
| 2003/0129677 | A1* | 7/2003 | Martens et al. ............ 435/7.23 |
| 2007/0104717 | A1* | 5/2007 | Pienta et al. ............. 424/155.1 |

FOREIGN PATENT DOCUMENTS

| EP | 1 157 041 B1 | 6/2005 |
| WO | WO 86/07062 | 12/1986 |
| WO | WO 90/04415 | 5/1990 |
| WO | 94/26787 | 11/1994 |
| WO | WO 94/26787 | 11/1994 |
| WO | 95/15982 | 6/1995 |
| WO | WO 95/15982 | 6/1995 |
| WO | 97/02479 | 1/1997 |
| WO | WO 97/02479 * | 1/1997 |
| WO | WO 97/04801 | 2/1997 |
| WO | 98/15833 | 4/1998 |
| WO | 98/16827 | 4/1998 |
| WO | WO 98/15833 | 4/1998 |
| WO | WO 98/16827 | 4/1998 |
| WO | WO 98/39659 | 9/1998 |
| WO | 98/50431 | 11/1998 |
| WO | WO 98/50431 | 11/1998 |
| WO | WO 99/43800 | 9/1999 |
| WO | 99/56129 | 11/1999 |
| WO | WO 99/56129 | 11/1999 |

OTHER PUBLICATIONS

Clark (Protein Engineering of Antibody Molecules for Prophylactic and Therapeutic Applications in Man, 1993, p. 1.*
Vollmers et al (Cancer, 1995, vol. 76, pp. 550-558).*
Hensel et al (Cancer Research, 1999, vol. 59, pp. 5299-5306).*
Varsano et al (Clin Exp Immunol, 1998, 113, pp. 173-182).*
Simpson et al, Am J Pathology, 1997, vol. 151, pp. 1455-1467.*
Aviv et al., "Purification of Biologically Active Globin Messenger RNA by Chromatography on Oligothymidylic Acid-Cellulose" *Proc. Natl. Acad. Sci. USA* 69(6):1408-1412 (Jun. 1972).
Baker et al., "Humanization of an anti-mucin antibody for breast and ovarian cancer therapy" *Advances in Experimental Medicine & Biology* 353:61-82 (1994).
Barratt-Boyes, S., "Making the most of mucin: a novel target for tumor immunotherapy" *Cancer Immunology, Immunotherapy* 43(3):142-151 (Nov. 1996).
Cai and Garen, "A melanoma-specific $V_H$ antibody cloned from a fusion phage library of a vaccinated melanoma patient" *Proc. Natl. Acad. Sci. USA* 93(13):6280-6285 (Jun. 25, 1996).
Cai and Garen, "Anti-melanoma antibodies from melanoma patients immunized with genetically modified autologous tumor cells: selection of specific antibodies from single-chain Fv fusion phage libraries" *Proc. Natl. Acad. Sci. USA* 92(14):6537-6541 (Jul. 3, 1995).
Cai and Garen, "Comparison of fusion phage libraries displaying $V_H$ or single-chain Fv antibody fragments derived from the antibody repertoire of a vaccinated melanoma patient as a source of melanoma-specific targeting molecules" *Proc. Natl. Acad. Sci. USA* 94(17):9261-9266 (Aug. 19, 1997).
Carter and Ridgway, "The next generation bispecific antibodies through domain interface engineering" *Antibody Engineering II: New Technology, Application, and Commercialization*, International Business Communications, Inc., Chapter 2.2, vol. 1:115-130 (1997).
Carter et al., "High level *Escherichia coli* expression and production of a bivalent humanized antibody fragment" *Bio/Technology* 10:163-167 (1992).
Carter et al., "Humanization of an anti-p185$^{HER2}$ antibody for human cancer therapy" *Proc. Natl. Acad. Sci.* 89:4285-4289 (May 1992).

(Continued)

*Primary Examiner*—Karen A. Canella
(74) *Attorney, Agent, or Firm*—Craig Svoboda, Esq.; Ginger R. Dreger, Esq.; Heller Ehrman LLP

(57) ABSTRACT

The present application describes a method for making antibodies which can be used for cancer diagnosis or therapy. The application also discloses a method for identifying an antigen which is differentially expressed on the surface of two or more distinct cell populations. The application additionally describes human antibodies directed against decay accelerating factor (DAF), as well as therapeutic compositions comprising such antibodies. Moreover, the application discloses a method of treating lung cancer with antibodies directed against DAF.

6 Claims, 5 Drawing Sheets

OTHER PUBLICATIONS

Chee et al., "Accessing genetic information with high-density DNA arrays" *Science* 274(5287):610-614 (Oct. 25, 1996).

Cheung et al., "Decay-accelerating factor protects human tumor cells from complement-mediated cytotoxicity in vitro" *Journal of Clinical Investigation* 81(4):1122-1128 (Apr. 1988).

Chirgwin et al., "Isolation of biologically active ribonucleic acid from sources enriched in ribonuclease" *Biochemistry* 18(24):5294-5299 (Nov. 27, 1979).

Christensen and Leslie, "Quantitative measurement of Fc receptor activity on human peripheral blood monocytes and the monocyte-like cell line, U937, by laser flow cytometry" *Journal of Immunological Methods* 132(2):211-219 (Sep. 14, 1990).

Couto et al., "Engineering of antibodies for breast cancer therapy: construction of chimeric and humanized versions of the murine monoclonal antibody BrE-3" *Advances in Experimental Medicine & Biology* 353:55-59 (1994).

Couto et al., "Humanization of KC4G3, an Anti-Human Carcinoma Antibody" *Hybridoma* 13:215-219 (1994).

de Kruif et al., "Rapid selection of cell subpopulation-specific human monoclonal antibodies from a synthetic phage antibody library" *Proc. Natl. Acad. Sci. USA* 92(9):3938-3942 (Apr. 25, 1995).

DeRisi et al., "Use of a cDNA microarray to analyse gene expression patterns in human cancer" *Nature Genetics* 14(4):457-460 (Dec. 1996).

Griffiths et al., "Isolation of High Affinity Human Antibodies Directly From Large Synthetic Repertoires" *EMBO Journal* 13:3245-3260 (1994).

Hamann et al., "The seven-span transmembrane receptor CD97 has a cellular ligand (CD55, DAF)" *Journal of Experimental Medicine* 184(3):1185-1189 (Sep. 1, 1996).

Hara et al., "A monoclonal antibody against human decay-accelerating factor (DAF, CD55), D17, which lacks reactivity with semen-DAF" *Immunology Letters* 37(2-3):145-152 (Aug. 1993).

Hara et al., "Levels of complement regulatory proteins, CD35 (CR1), CD46 (MCP) and CD55 (DAF) in human haematological malignancies" *British Journal of Haematology* 82(2):368-373 (Oct. 1992).

Hayes, D., "Should we treat HER, too?" *Journal of Clinical Oncology* 14(3):697-699 (Mar. 1996).

Henderikx et al., "Human single-chain Fv antibodies to MUC1 core peptide selected from phage display libraries recognize unique epitopes and predominantly bind adenocarcinoma" *Cancer Research* 58(19):4324-4332 (Oct. 1, 1998).

Hensel et al., "Characterization of glycosylphosphatidylinositol-linked molecule CD55/decay-accelerating factor as the receptor for antibody SC-1-induced apoptosis" *Cancer Research* 59(20):5299-5306 (Oct. 15, 1999).

Hibi et al., "Serial analysis of gene expression in non-small cell lung cancer" *Cancer Research* 58(24):5690-5694 (Dec. 15, 1998).

Huls et al., "A recombinant, fully human monoclonal antibody with antitumor activity constructed from phage-displayed antibody fragments" *Nature Biotechnology* 17(3):276-281 (Mar. 1999).

Kaminski et al., "Iodine-131-anti-B1 radioimmunotherapy for B-cell lymphoma" *Journal of Clinical Oncology* 14(7):1974-1981 (Jul. 1996).

Kaminski et al., "Radioimmunotherapy of B-cell Lymphoma with ($^{131}$I) Anti-B1 (Anti-CD20) Antibody" *New England J. of Medicine* 329:459-465 (1993).

Koretz et al., "Decay-accelerating factor (DAF, CD55) in normal colorectal mucosa, adenomas and carcinomas" *British Journal of Cancer* 66(5):810-814 (Nov. 1992).

Liang and Pardee, "Recent advances in differential display" *Current Opinion in Immunology* 7(2):274-280 (Apr. 1995).

Lublin et al., "Biosynthesis and Glycosylation of the Human Complement Regulatory Protein Decay-Accelerating Factor" *Journal of Immunology* 137(5):1629-1635 (1986).

Maloney et al., "IDEC-C2B8 (Rituximab) anti-CD20 monoclonal antibody therapy in patients with relapsed low-grade non-Hodgkin's lymphoma" *Blood* 90(6):2188-2195 (Sep. 15, 1997).

Marks et al., "By-passing immunization: human antibodies from V-gene libraries displayed on phage" *J. Mol. Biol.* 222:581-597 (1991).

Marks et al., "Human antibody fragments specific for human blood group antigens from a phage display library" *Bio/Technology* 11(10):1145-1149 (Oct. 1993).

McCafferty et al., "Phage antibodies: filamentous phage displaying antibody variable domains" *Nature* 348:552-554 (1990).

McLaughlin et al., "Rituximab chimeric anti-CD20 monoclonal antibody therapy for relapsed indolent lymphoma: half of patients respond to a four-dose treatment program" *Journal of Clinical Oncology* 16(8):2825-2833 (Aug. 1998).

Merchant et al., "An efficient route to human bispecific IgG" *Nature Biotechnology* 16(7):677-681 (Jul. 1998).

Nicholson-Weller and Wang, "Structure and function of decay accelerating factor CD55" *Journal of Laboratory & Clinical Medicine* 123(4):485-491 (Apr. 1994).

Niehans et al., "Human carcinomas variably express the complement inhibitory proteins cD46 (membrane cofactor protein), CD55 (decay-accelerating factor), and CD59 (protectin)" *American Journal of Pathology* 149(1):129-142 (Jul. 1996).

Nissim et al., "Antibody fragments from a 'single pot' phage display library as immunochemical reagents" *EMBO Journal* 13(3):692-698 (1994).

Portolano et al., "High affinity, thyroid-specific human autoantibodies displayed on the surface of filamentous phage use V genes similar to other autoantibodies" *Journal of Immunology* 151(5):2839-2851 (Sep. 1, 1993).

Press et al., "Phase II trial of $^{131}$I-B1 (anti-CD20) antibody therapy with autologous stem cell transplantation for relapsed B cell lymphomas" *Lancet* 346(8971):336-340 (Aug. 5, 1995).

Press et al., "Radiolabeled-antibody Therapy of B-cell Lymphoma with Autologous Bone Marrow Support" *New England J. of Medicine* 329:1219-1224 (1993).

Reff et al., "Depletion of B cells in vivo by a chimeric mouse human monoclonal antibody to CD20" *Blood* 83(2):435-445 (Jan. 15, 1994).

Ridgway et al., "Identification of a human anti-CD55 single-chain Fv by subtractive panning of a phage library using tumor and nontumor cell lines" *Cancer Research* 59(11):2718-2723 (Jun. 1, 1999).

Riethmuller et al., "Monoclonal antibody therapy for resected Dukes' C colorectal cancer: seven-year outcome of a multicenter randomized trial" *Journal of Clinical Oncology* 16(5):1788-1794 (May 1998).

Riethmuller et al., "Randomised trial of monoclonal antibody for adjuvant therapy of resected Dukes' C colorectal carcinoma" *Lancet* 343 (8907):1177-1183 (May 14, 1994).

Schena et al., "Quantitative monitoring of gene expression patterns with a complementary DNA microarray" *Science* 270:467-470 (1995).

Seed and Aruffo, "Molecular cloning of the CD2 antigen, the T-cell erythrocyte receptor, by a rapid immunoselection procedure" *Proc. Natl. Acad. Sci. USA* 84(10):3365-3369 (May 1987).

Sheets et al., "Efficient construction of a large nonimmune phage antibody library: the production of high-affinity human single-chain antibodies to protein antigens" *Proc. Natl. Acad. Sci. USA* 95(11):6157-6162 (May 26, 1998).

Suva et al., "A parathyroid hormone-related protein implicated in malignant hypercalcemia: cloning and expression" *Science* 237(4817):893-896 (Aug. 1987).

Tzahar and Yarden, "The ErbB-2/HER2 oncogenic receptor of adenocarcinomas: from orphanhood to multiple stromal ligands" *Biochimica et Biophysica Acta* 1377(1):M25-M37 (Feb. 20, 1998).

van Ewijk et al., "Subtractive isolation of phage-displayed single-chain antibodies to thymic stromal cells by using intact thymic fragments" *Proc. Natl. Acad. Sci. USA* 94(8):3903-3908 (Apr. 15, 1997).

Vaughan et al., "Human Antibodies With Sub-nanomolar Affinities Isolated From a Large Non-immunized Phage Display Library" *Nature Biotechnology* 14:309-314 (1996).

Voldborg et al., "Epidermal growth factor receptor (EGFR) and EGFR mutations, function and possible role in clinical trials" *Annals of Oncology* 8(12):1197-1206 (Dec. 1997).

Vollmers et al., "Adjuvant therapy for gastric adenocarcinoma with the apoptosis-inducing human monoclonal antibody SC-1: first clinical and histopathological results" *Oncology Reports* 5(3):549-552 (May-Jun. 1998).

Vollmers et al., "Apoptosis of stomach carcinoma cells induced by a human monoclonal antibody" *Cancer* 76(4):550-558 (Aug. 15, 1995).

Vollmers et al., "SC-1, a functional human monoclonal antibody against autologous stomach carcinoma cells" *Cancer Research* 49(9):2471-2476 (May 1, 1989).

Zhang et al., "Gene expression profiles in normal and cancer cells" *Science* 276:1268-1272 (1997).

Hall et al., "A novel tumor-specific human single-chain Fv selected from an active specific immunotherapy phage display library" *Immunotechnology* 4(2):127-140 (Oct. 1998).

Hoogenboom et al., "Antibody phage display technology and its applications" *Immunotechnology* 4(1):1-20 (Jun. 1998).

Hoogenboom, "Designing and optimizing library selection strategies for generating high-affinity antibodies" *Trends in Biotechnology* 15(2):62-70 (Feb. 1997).

Varsano et al., "Human lung cancer cell lines express cell membrane complement inhibitory proteins and are extremely resistant to complement-mediated lysis: a comparison with normal human respiratory epithelium in vitro, and an insight into mechanism(s) of resistance" *Clin Exp Immunol* 113:173-182 (1998).

Paul, Fundamental Immunology, Raven Press NY, chapter 8, p. 242, 1993.

Murphy et al., Clinical Oncology, ACS, p. 285, 1995.

Hall et al., "A Novel Tumor-Specific Human Single-Chain Fv Selected From An Active Specific Immunotherapy Phage Display Library", Immunotechnology, 4(2):127-40, 1998, XP004193637.

Hoogenboom et al., "Antibody Phage Display Technology and Its Applications", Immunotechnology, 4(1):1-20, 1998, XP002105422.

Hoogenboom et al., "Designing and Optimizing Library Selection Stragies for Generating High-Affinity Antibodies", Trends in Biotechnology, 15(2):626-70, 1997, XP004034115.

Varsano et al., "Human Lung Cancer Cell Lines Express Cell Membrane Complement Inhibitory Proteins and are Extremely Resistant to Complement-Mediated Lysis; A Comparison with Normal Human Respiratory Epithelium in Vitro, And An Insight Into Mechanism(s), of Resistance", Clinical and Experimental Immunology, 113(2):173-82, 1998, XP000925221.

U.S. Appl. No. 60/082,953, filed Apr. 1998, Marks, J., et al.

U.S. Appl. No. 09/249,529, filed Feb. 1999, Marks, J.D., et al.

Hynes, N.E., et al., "Overexpression of the c-erbB-2 Protein in Human Breast Tumor Cell Lines," *J. Cell. Biochem.*—*39*:167:173 (1989).

Marks, J.D., et al., "Human Antibody Fragments Specific for Human Blood Group Antigens From a Phase Display Library," *Bio/Technology*—*11*:1145-1149 (1993).

Hoogenboom, H.R., et al., "Antibody Phage Display Technology and its Applications," *Immunotechnology*—*4*:1-20 (1998).

Hoogenboom, H.R., "Designing and Optimizing Library Selection Strategies for Generating High-Affinity Antibodies," *Trends Biotechnol.*—*15*:62-70 (Feb. 1997).

de Haard, H., et al., "Creating and Engineering Human Antibodies for Immunotherapy," *Adv. Drug Deliv. Rev.*—*31*:5-31 (1998)

Carter and Ridgway, Antibody Engineering II: New Technology, Application and Commercialization, vol. II, IBC USA Publishing, Southborough, MA pp. 115-130 (Dec. 1997).

Pereira, S., et al., "A Model System for Detection and Isolation of a Tumor Cell Surface Antigen Using Antibody Phage Display" *J. Immunol. Methods*—*203*:11-24 (1997).

Pelsers, M.M.A.L., et al., "A Sensitive Immunoassay for Rat Fatty Acid Translocase (CD36) Using Phase Antibodies Selected on Cell Transfectants: Abundant Presence of Fatty Acid Translocase/CD36 in Cardiac and Red Skeletal Muscle and Up-Regulation in Diabetes," *Biochem. J*—*337*:407-414 (1999).

Osbourn, J.K., et al., "Pathfinder Selection: in situ Isolation of Novel Antibodies," *Immunotechnology*—*3*:293-302 (1998).

Meulemans, E.V., et al., "Selection of Phage-Display Antibodies Specific for a Cytoskeletal Antigen by Competitive Elution With a Monoclonal Antibody," *J. Mol. Biol.*—*244*:353-360 (1994).

Pereira, S., et al., "Combinatorial Antibodies Against Human Malignant Melanoma," *Hybridoma*—*16*(1):11-16 (1997).

Cai, X., et. al., "Comparison of Fusion Phage Libraries Displaying of V$_H$ or Single-Chain Fv Antibody Fragments Derived From the Antibody Repertoire of a Vaccinated Melanoma Patient as a Source of Melanoma-Specific Targeting Molecules," *Proc. Natl. Acad. Sci. USA*—*94*:9261-9266 (1997).

Phage Display of Peptides and Proteins: A Laboratory Manual (1996), Eds.: Kay, Winter and McCafferty, Academic Press Inc., London/San Diego.

Vaughan, T.J., et al., "Human Antibodies With Sub-Nanomolar Affinities Isolated From a Large Non-Immunized Phage Display Library," *Nature Biotech.*—*14*:309-314 (1996).

Sheets, M.D., et al., "Efficient Construction of a Large Nominnune Phage Antibody Library: The Production of High-Affinity Human Single-Chain Antibodies to Protein Antigens" *Proc. Natl. Acad. Sci. USA*—95:6157-6162 (1998).

Schlom, Biologica Therapy of Cancer (1991), Chapter 21, pp. 464-481, Eds.: De vita, Hellman and Rosenberg, Lippincott, Philadelphia.

Bradbury, A., et al., "Use of Living Columns to Select Specific Phage Antibodies," *Bio/Technology*—*11*:1565-1569 (1993).

Herlyn, D., et al., "Identification of Tumor Antigens Using Antibody Phage Display," Antibody Engineering: New Technologies, Applications and Commercialization (Eds.: Thibeault and Savage), IBC USA Publishing, Southborough, MA pp. 91-102 (Jul. 1996).

Topping, K.P., et al., "Isolation of Anti-Colorectal Tammour Antiboides From a Phage-Display Library" *Biochem. Soc. Trans.*—*25*:2685 (1997).

Noronha, E.J., et al., "Limited Diversity of Human scFv Fragments Isolated by Panning a Synthetic Phage-Display scFv Library With Cultured Human Melanoma Cells," *J. Immunol.*—*161*:2968-2976 (1998).

Molecular Cloning: A Laboratory Manual (1989), Second Edition, Eds.: Sambrook, Fritsch and Maniatis, Cold Spring Harbor Laboratory Press, New York.

Nunc Tech Note, vol. 1 No. 3 (1993).

U.S. Appl. No. 60/082,953, filed Apr. 24, 1998, Marks et al.

U.S. Appl. No. 09/249,529, filed Feb. 12, 1999, Marks et al.

Hynes et al., "Overexpression of the c-erb Protein in Human Breast Tumor Cell Lines", Journal of Cellular Biochemistry 39:167-173 (1989).

de Haard et al., "Creating and Engineering Human Antibodies for Immunotherapy", Advanced Drug Delivery Reviews 31:5-31 (1998).

Pereira et al., "A Model System for Detection and Isolation of a Tumor Cell Surface Antigen Using Antibody Phage Display", Journal of Immunological Methods, 203:11-24 (1997).

Pelsers et al., "A Sensitive Immunoassay for Rat Fatty Acid Translocase (CD36) using Phage Antibodies Selected on Cell Transfectants: Abundant Presence of Fatty Translocase/CD36 in Cardiac and Red Skeletal Muscle and Up-Regulation in Diabetes", Biochem J. 337:407-414 (1999).

Osbourn et al., "Pathfinder Selection: In Situ Isolation of Novel Antibodies", Immunotechnology 3:293-302 (1998).

Meulemans, et al., "Selection of Phage-Displayed Antibodies Specific for a Cytoskeletal Antigen by Competitive Elution with a Monoclonal Antibody", J. Mol. Biol. 244:353-360 (1994).

Pereira et al., "Combinatorial Antibodies Against Human Malignant Melanoma", Hybridoma, vol. 16, 1:11-16 (1997).

J. Schlom, Biologic Therapy of Cancer, (1991), Chpt. 21, pp. 464-481; Eds.: De Vita, Hellman and Rosenberg, Lippincott, Philadelphia.

Bradbury et al., "Use of Living Columns to Select Specific Phage Antibodies", Bio/Technology, 11:1565-1569 (1993).

Heryln et al., Antibody Engineering; New Technologies, Applications and and Commericilization (Eds.: thibeault and Savage), IBC USA Publishing, Southborough, MA, pp. 91-102 (publication date Jul. 1996).

Topping et al., "Isolation of Anti-Colorectal Tumour Antibodies from a Phage-Display Library" Biochemical Society Transactions, pp. 25 (1997).

Noronha et al., "Limited Diversity of Human scFv Fragments Isolated by Panning a Synthetic Phage-Display scFc Library with Cultured Human Melanoma Cells", J. Immunol., 161:2968-2976 (1998).

Nunc Tech Note, vol. 1, No. 3 (1993).

Molecular Cloning: A Laboratory Manual (1989), Second Edition, Eds., Sambrook, Fritsch and Manlatis, Cold Spring Harbor Laboratory Press, New York.

* cited by examiner

Fig. 5A: Alignment of VL domains of human anti-DAF antibodies

```
LU30   1 QSVLTQPPSASGSPGQSVTISCTG[TSSDVGGYNYV]SWYQQHPGKAPKEMI
LU13   1 QSVLTQPASVSGSPGQSITVSCTG[TSSDVGGYNYV]SWYQQHPGKAPKLMI
LU20   1 DIQMTQSPSTLSASIGDRVTITCRA[SEGIY---HWL]AWYQQKPGKAPKLLI

LU30  51 Y[DVS]KRPSGVSNRFSGSKSGNTASLTISGVQAEDEADYCSS[YTSASTV]I
LU13  51 Y[EGS]KRPSGVSNRFSGSKSGNTASLTISGLQAEDEADYCSS[YTTRSTR]V
LU20  49 Y[KAS]SLASGAPSRFSGSGSGTDFTLTISSLQPDDFATYYCQQ[YS-NYPL]T

LU30 101 FGGGTKLTVL  (SEQ ID NO:1)
LU13 101 FGGGTKLTVL  (SEQ ID NO:2)
LU20  99 FGGGTKLEIK  (SEQ ID NO:3)
```

Fig. 5B: Alignment of VH domains of anti-DAF antibodies

```
LU30   1 QVKLQESGGGLVQPGGSLKLSCAAS[GFTFSGY]GMSWIRQTPDKRLEWVAT
LU13   1 QVQLQESGGNLVQPGGSLRLSCAAS[GFTFSSY]AMSWVRQAPGKGLEWVSA
LU20   1 EVQLVETGGGLVQPGRSLRLSCAAS[GFTFEDY]GMHWVRQAPGKGLEWVSG

LU30  51 IN[SGGS]YTYYSDSVKGRFTISRDNVKNTLYLQMSSLKSEDTAMYYCARR[N
LU13  51 IS[GSGG]NTYYADSVKGRFTISRDNSKNTLYLQMNTLRAEDTAVYYCARR[A
LU20  51 IN[WNGG]STGYADSVKGRFTISRDNAKNSLYLQMNSLRAEDTALYYCARD[A

LU30 101 GTLY-YYLMD]YWGRGTLVTVSS  (SEQ ID NO:4)
LU13 101 ------SYD]YWGQGTMVTVSS   (SEQ ID NO:5)
LU20 101 PSGSYGYWFD]PWGQGTLVTVSS  (SEQ ID NO:6)
```

ANTIBODIES FOR CANCER THERAPY AND DIAGNOSIS

This application is a divisional application of U.S. application Ser. No. 09/515,825, filed on Feb. 29, 2000 now abandoned, incorporated herein by reference, and to which priority is claimed under 35 U.S.C. § 120, which co-pending application is a non-provisional application filed under 37 C.F.R. 1.53(b)(1) which claims priority under 35 U.S.C. 119(e) to provisional application number 60/122,262 filed Mar. 1, 1999, the contents of which are incorporated herein by reference.

BACKGROUND OF THE INVENTION

1. Field of the Invention

The present invention concerns a method for making antibodies which can, for example, be used for cancer diagnosis or therapy. The invention further provides a method for identifying an antigen which is differentially expressed on the surface of distinct cell populations. The present invention additionally provides human antibodies directed against decay accelerating factor (DAF), as well as therapeutic compositions comprising such antibodies. Moreover, the invention pertains to a method of treating lung cancer with antibodies directed against DAF.

2. Description of Related Art

The demonstration of significant anti-tumor efficacy of antibodies has long been sought-after in the clinic and recently obtained using "naked" chimeric/humanized antibodies (Riethmüller et al., *Lancet*, 343: 1177-1183 (1994); Riethmüller et al., *J. Clin. Oncol.*, 16: 1788-1794 (1998); Maloney et al., *Blood*, 90: 2188-2195 (1997); McLaughlin et al., *J. Clin. Oncol.*, 16: 2825-2833 (1998); and Baselga et al., *J. Clin. Oncol.*, 14: 697-699 (1996)) antibodies as well as with radiolabeled murine antibodies (Press et al., *N. Engl. J. Med.*, 329: 1219-1224 (1993); Press et al., *Lancet*, 346: 336-340, (1995); Kaminski et al., *N. Engl. J. Med.*, 329: 459-495 (1993); Kaminski et al., *J. Clin. Oncol.*, 14: 1974-1981 (1996)). Indeed a chimeric anti-CD20 antibody (Reff et al., *Blood*, 83: 435-445 (1994)) and a chimeric/humanized anti-HER2 antibody (Carter et al. *PNAS (USA)* 89:4285-4289 (1992)) have recently been approved by US Federal Drug Administration for the treatment of non-Hodgkin's lymphoma and metastatic breast cancer, respectively. These successes with anti-tumor antibodies in patients has led to renewed interest in the identification of novel tumor-associated antigens suitable for antibody targeting.

The traditional approach to obtaining tumor-specific antibodies has been to immunize mice with tumor cells and to screen the resultant monoclonal antibodies for their binding specificity. Unfortunately tumor-binding antibodies obtained in this way often cross-react with many normal cells, which may interfere with their clinical utility. Ideally one would like to select rather than screen for antibodies that bind selectively to tumor. The advent of antibody fragment display on phage (McCafferty et al., *Nature*, 348: 552-554 (1990)) and the development of large (>$10^{10}$ clone) phage display libraries (Griffiths et al., *EMBO J.*, 13:3245-3260 (1994), Vaughan et al. *Nat. Biotechnol.* 14: 309-314 (1996)) offers a potential way of making antibodies. With antibody phage screening, unlike hybridoma technology, it is readily possible to obtain antibodies binding antigens that are highly conserved between mouse and man (Nissim et al., *EMBO J.*, 13:692-698 (1994)).

Naïve antibody phage libraries have proved to be a rapid and general method for identifying antibodies binding to purified antigens (Griffiths et al., *EMBO J.*, 13:3245-3260 (1994); Vaughan et al. *Nat. Biotechnol.* 14: 309-314 (1996); Nissim et al., *EMBO J.*, 13:692-698 (1994)). In contrast, panning cellular targets with antibody phage has proved much more difficult because of the much lower effective antigen concentration, greater antigen complexity and the tendency of phage to bind non-specifically to cells. Nevertheless, antibodies against cell surface antigens have been identified (Marks et al, *Bio/Technol.*, 11: 1145-1149 (1992); Portolano et al., *J. Immunol.*, 151:2839-2851 (1993); de Kruif et al, *Proc. Natl. Acad. Sci. USA*, 92:3938-3942 (1995); Van Ewijk et al., *Proc. Natl. Acad. Sci. USA*, 94:3903-3908 (1997); Cai et al, *Proc. Natl. Acad. Sci. USA*, 92:6537-6541 (1995); Cai et al *Proc. Natl. Acad. Sci. USA*, 93:6280-6285 (1996); Cai et al, *Proc. Natl. Acad. Sci. USA*, 94:9261-9266 (1997)). Melanoma specific antibodies have been identified by selecting for antibody phage that bind to melanoma cells but not melanocytes using antibody phage libraries constructed from human donors immunized with their own tumor cells (Cai et al, *Proc. Natl. Acad. Sci. USA*, 92:6537-6541 (1995); Cai et al *Proc. Natl. Acad. Sci. USA*, 93:6280-6285 (1996); Cai et al., *Proc. Natl. Acad. Sci. USA*, 94:9261-9266 (1997)).

Decay Accelerating Factor (DAF), is a GPI-anchored protein that acts together with two other GPI-anchored proteins, CD46 and CD59, in protecting host cells from complement-mediated cell lysis (Nicholson-Weller et al. *J. Lab. Clin. Med.*, 123:485-491 (1994)). DAF is expressed at widely varying levels on tumor cell lines and its overexpression correlates with enhanced resistance to complement-mediated cell lysis in vitro (Cheung et al., *J. Clin. Invest.*, 81:1122-1128 (1988)). DAF overexpression has been observed on a variety of human tumor tissues including 6/9 lung adenocarcinomas and 2/7 lung squamous cell carcinomas (Niehans et al., *Am. J. Path.*, 149:129-142 (1996)). Regarding normal lung tissue, DAF has been detected by immunohistochemistry on the alveolar epithelium, interstitium and endothelium as well as the bronchial epithelium, glands and ducts plus blood vessels (Niehans et al., *Am. J. Path.*, 149:129-142 (1996)).

Other publications relating to DAF include Hara et al. *Immunology Letters* 37:145-152 (1993); Nicholson-Weller and Wang *J. Lab. Clin. Med.* 123(4):485491 (1994); Lublin et al. *J. Immunol.* 137:1629-1635 (1986); WO99/43800; WO98/39659; U.S. Pat. No. 5,695,945; U.S. Pat. No. 5,763,224; and WO 86/07062.

Vollmers et al. *Cancer Research* 49: 2471-2476 (1989); and Vollmers et al. *Cancer* 76(4): 550-558 (1995) describe the human IgM monoclonal antibody "SC-1" which is said inhibit growth of stomach adenocarcinoma cells in vitro and in vivo by inducing apoptosis. Vollmers et al. *Oncology Reports* 5:549-552 (1998) reports the results of a clinical trial in which patients with poorly differentiated stomach adenocarcinoma were treated with the SC-1 antibody. The later publication, Hensel et al. *Cancer Research* 59:5299-5306 (1999), identifies DAF as the antigen bound by SC-1.

SUMMARY OF THE INVENTION

In the present application, a large naïve antibody phage library was used to search for cancer-associated antigens, thus obviating the need for creating custom libraries from immunized donors. In addition, antibodies were selected using live rather than fixed cells, to obtain antibodies primarily against native rather than denatured antigens. This was done to facilitate subsequent expression cloning of corresponding antigen as well as enhance the therapeutic potential of antibodies obtained. Indeed an antigen corresponding to a scFv fragment identified with significant tumor selectivity was cloned according to the present methods.

Accordingly, the invention provides a method for making an antibody comprising the following steps: (a) binding antibody phage from a naïve antibody phage library to a live cancer cell; (b) selecting an antibody phage or antibody which binds selectively to the live cancer cell; and (c) identifying an antigen to which the antibody phage or antibody binds.

The invention further provides an antibody derived according to the method of the preceding paragraph and optionally including amino acid sequence alterations (e.g. additions, deletions and/or substitutions) compared to the antibody selected in step (b)). Moreover, the invention provides a method for detecting the antigen comprising exposing a sample suspected of containing the antigen to the antibody or altered antibody and determining binding of the antibody or altered antibody to the sample. The invention further provides a method for treating a mammal having a disease or disorder comprising administering the above antibody or altered antibody to the mammal in an amount effective to treat the disease or disorder.

The invention further provides a method for identifying an antigen which is differentially expressed on the surface of two or more distinct cell populations, comprising the following steps: (a) binding antibody phage from a naïve antibody phage library to a first cell population; (b) binding the antibody phage to a second cell population which is distinct from the first cell population; (c) selecting an antibody phage or antibody which binds selectively to the first cell population; and (d) identifying an antigen to which the antibody phage or antibody in (c) binds.

The invention further provides an antagonist, such as an antibody, directed against an antigen, wherein the antigen has been identified according to the method of the previous paragraph.

The invention additionally relates to an isolated human antibody which is directed against, or specifically binds to, human decay accelerating factor (DAF), obtainable by the methods herein. The invention further provides a human antibody which has better binding affinity for DAF than the human IgM SC-1 antibody has for DAF, e.g. about 10 nM or better binding affinity for human DAF (for instance, in the range from about 10 nM to about 1 pM). An example of an antibody with such strong binding affinity for DAF is the LU30 antibody herein which has a binding affinity ($K_d$) for DAF of about 13 nM as determined using a BIACORE™ instrument. The antibody optionally binds an epitope on DAF bound by the LU30, LU13 or LU20 antibodies herein disclosed. The human antibody may, for instance, comprise antigen-binding amino acid residues of the LU30, LU13 or LU20 antibodies. The application additionally provides the human antibodies designated LU30, LU13 and LU20 herein as well as variants of any one of those antibodies. Preferred amino acid sequence variants comprise VH and VL domains which together share about 90-100%, and preferably about 95-100%, and most preferably 98-100%, amino acid sequence identity with the VH and VL amino acid sequences of the LU30, LU13 or LU20 antibodies as depicted in FIGS. 5A and 5B herein. One preferred amino acid sequence variant is an affinity matured variant, which comprises one or more amino acid sequence modifications (e.g. about 1-20, and most preferably about 3-10 amino acid substitutions) in one or more hypervariable regions of the LU30, LU13 or LU20 VH and/or VL amino acid sequences disclosed herein.

Another type of variant is a glycosylation variant which has altered glycosylation compared to a parent antibody and thus may have altered effector function(s). While Fv fragment forms (e.g. single chain Fv fragments, scFv) of the LU30, LU13 or LU20 antibodies may be used, the variable regions of these antibodies are optionally fused to heterologous polypeptide(s) such as (1) a toxin polypeptide(s) to generate an immunotoxin or (2) antibody constant region sequences to make larger antibody molecules, such as Fab fragments, F(ab')$_2$ fragments or intact antibodies. Such intact antibodies generally have human heavy and light chain constant regions and, therefore, have antibody effector functions, such as antibody-dependent cell-mediated cytotoxicity (ADCC) and complement dependent cytotoxicity (CDC).

In another embodiment, the invention pertains to a pharmaceutical composition comprising a human antibody directed against DAF and a pharmaceutically acceptable carrier. In addition, the invention provides an article of manufacture comprising the pharmaceutical composition and a package insert instructing the user of the composition to treat a patient having, or predisposed to, lung cancer with the composition. The lung cancer to be treated includes small-cell lung cancer, non-small cell lung cancer, large cell lung carcinoma, lung adenocarcinoma, and squamous cell lung carcinoma.

In yet a further embodiment, the invention relates to method of treating lung cancer comprising administering a therapeutically effective amount of an antibody directed against decay accelerating factor (DAF) to a human patient. Candidates for treatment with the anti-DAF antibody are optionally screened to determine DAF expression by tumor cells. For instance, DAF overexpression, and/or expression of a DAF glycoform, by the tumor may be assessed using diagnostic procedures available in the art, such as immunohistochemistry (IHC) or a DNA-based assay (e.g. fluorescent in situ hybridization, FISH). This way, a subpopulation of cancer patients (e.g. DAF-overexpressing patients or patients expressing a cancer-related variant of DAF) may be identified and those patients can be treated as described herein. The antibody may be administered in the neoadjuvant, adjuvant or metastatic settings. Moreover, the antibody used for such therapy may be conjugated with a cytotoxic agent (examples of which are provided below) in order to generate an immunotoxin. Preferably, the antibody is a human antibody (e.g. one which has a binding affinity for DAF of about 10 nM or better). The antibody for such therapy optionally binds an epitope on DAF bound by any one of the LU30, LU13, LU20, 791T36 or SC-1 antibodies. The antibody for therapy may, therefore, comprise antigen-binding amino acid residues of the LU30, LU13, LU20, 791T36 or SC-1 antibodies. The patient may optionally be treated with a second different cytotoxic agent, wherein the second cytotoxic agent is therapeutically effective against lung cancer. Examples of such second cytotoxic agents include, but are not limited to, navelbine, gemcitabine, a taxoid, carboplatin, cisplatin, etoposide, cyclophosphamide, mitomycin, vinblastine, an anti-ErbB2 antibody (e.g. HERCEPTIN®, sold by Genentech, Inc., South San Francisco), an anti-angiogenic factor antibody (e.g. an anti-VEGF antibody), an anti-mucin antibody, or a second antibody directed against a different epitope on DAF. Such therapy with the combination of the antibody and the second cytotoxic agent may result in a synergistic therapeutic effect against lung cancer.

BRIEF DESCRIPTION OF THE DRAWINGS

FIGS. 5A and 5B depict the amino acid sequences of the variable light (VL) (FIG. 5A; SEQ ID NOS: 1-3, respectively) and variable heavy (VH) (FIG. 5B; SEQ ID NOS: 4-6, respectively) domains of human antibodies LU30, LU13 and LU20 identified in Example 1. Complementarity Determining Region (CDR) residues are those residues in bold and hypervariable loop residues are within brackets.

TABLE 1

Primary screening of scFv phage clones

Figure 1:
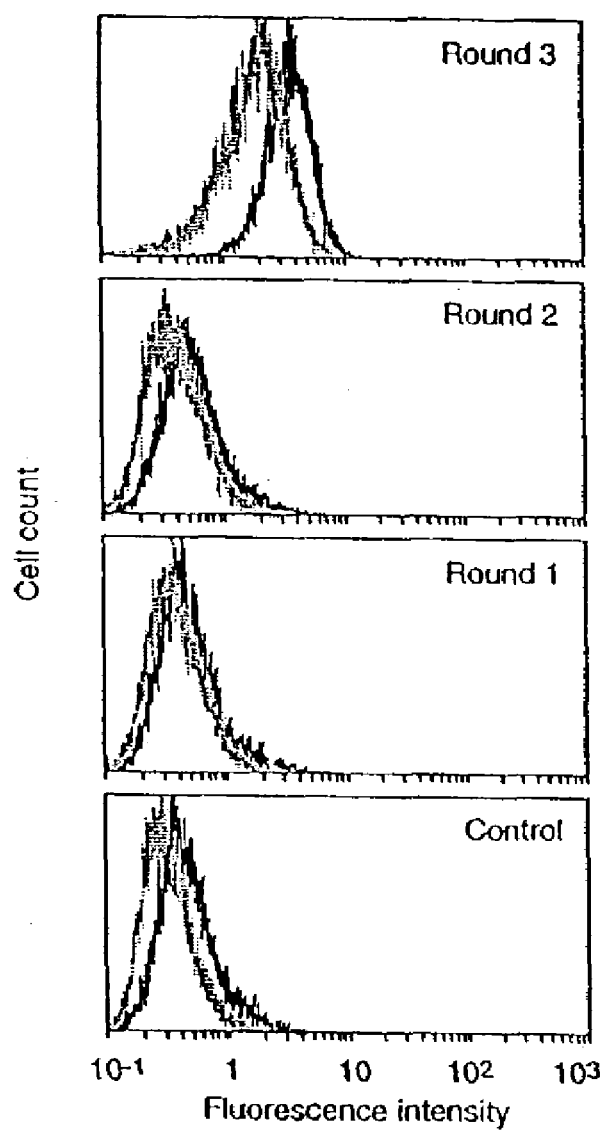
FIG. 1 depicts flow cytometric analysis of phage populations from rounds 1, 2 and 3 binding to tumor cell line 1264 (dark) used for selection and non-tumor cell line BEAS-2B (light) used for counter-selection. Also shown is a negative control phage population.

| BstNI fingerprint type | # tumor selective clones[a] | clone identity (# clones sequenced) |
|---|---|---|
| 1 | 110 | LU4 (8) |
| 2 | 49 | LU1 (7) |
| 3 | 10 | LU20 (9) |
| 4 | 7 | LU13 (3), LU34 (4)[b] |
| 5 | 4 | LU22 (4) |
| 6 | 3 | LU36 (3) |
| 7 | 3 | LU41 (3) |
| 8 | 3 | LU57 (2) |
| 9 | 3 | LU3 (1), LU77 (2)[b] |
| 10 | 2 | LU30 (2) |
| 11 | 1 | LU7 (1) |
| 12 | 1 | LU71 (1) |
| 13 | 1 | LU100 (1) |
| 14 | 1 | LU60 (1)[c] |
| 15 | 1 | LU78 (1) |

[a]Tumor selective clones by phage ELISA: robust binding to 1264 cells ($A_{450}$-$A_{650}$ ≧0.3) and much weaker binding to BEAS-2B cells (≧10-fold lower signal), as judged by phage ELISA.
[b]Clones LU13 and LU34 are predicted from their nucleotide sequences to generate identical fingerprint patterns, whereas clones LU3 and LU77 share closely related fingerprints that were not distinguishable by our electrophoretic analysis.
[c]Codon 3 in $V_H$ is amber (TAG) that will be read through as glutamine in the supE *E. coli* strain, TG1.

DETAILED DESCRIPTION OF THE PREFERRED EMBODIMENTS

I. Definitions

The term "antibody" is used in the broadest sense and specifically covers intact monoclonal antibodies, polyclonal antibodies, multispecific antibodies (e.g. bispecific antibodies) formed from at least two intact antibodies, and antibody fragments so long as they exhibit the desired biological activity.

"Antibody fragments" comprise a portion of an intact antibody, preferably the antigen binding or variable region of the intact antibody. Examples of antibody fragments include Fab, Fab', F(ab')$_2$, and Fv fragments; diabodies; "linear antibodies" (U.S. Pat. No. 5,641,870); single-chain antibody molecules such as single chain Fv fragments (scFv); and multispecific antibodies formed from antibody fragments.

An "intact" antibody is one which comprises an antigen-binding variable region as well as a tight chain constant domain ($C_L$) and heavy chain constant domains, $C_H1$, $C_H2$ and $C_H3$. The constant domains may be native sequence constant domains (e.g. human native sequence constant domains) or amino acid sequence variants thereof. Preferably, the intact antibody has one or more effector functions.

Antibody "effector functions" refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g. B cell receptor, BCR), etc.

Depending on the amino acid sequence of the constant domain of their heavy chains, intact antibodies can be assigned to different "classes". There are five major classes of intact antibodies: IgA, IgD, IgE, IgG, and IgM, and several of these may be further divided into "subclasses" (isotypes), e.g., IgG1 (including human A and non-A allotypes), IgG2, IgG3, IgG4, IgA, and IgA2. The subunit structures and three-dimensional configurations of different classes of immunoglobulins are well known.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcgammaRIII only, whereas monocytes express FcgammaRI, FcgammaRII and FcgammaRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1998).

"Complement dependent cytotoxicity" or "CDC" refer to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods* 202:163 (1996), may be performed.

The "antigen-binding" amino acid residues of an antibody are those residues which contact antigen and result in specific binding of the antibody to that antigen. Generally, the antigen-binding residues coincide with the hypervariable region residues of an antibody. The hypervariable regions generally comprise amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed.

Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 (1975), or may be made by recombinant DNA methods (see, e.g., U.S. Pat. No. 4,816,567). The "monoclonal antibodies" may also be isolated from phage antibody libraries.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al, *Proc. Natl. Acad. Sci. USA*, 81:6851-6855 (1984)).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art. In the preferred embodiment, the human antibody is selected from a phage library, where that phage library expresses human antibodies (Vaughan et al. *Nature Biotechnology* 14:309-314 (1996): Sheets et al *PNAS (USA)* 95:6157-6162 (1998)); Hoogenboom and Winter, *J. Mol. Biol.*, 227:381 (1991); Marks et al, *J. Mol. Biol.*, 222:581 (1991); and Example 1 herein). Human antibodies can also be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al, *Bio/Technology* 10: 779-783 (1992); Lonberg et al., *Nature* 368: 856-859 (1994); Morrison, *Nature* 368:812-13 (1994); Fishwild et al., *Nature Biotechnology* 14: 845-51 (1996); Neuberger, *Nature Biotechnology* 14: 826 (1996); Lonberg and Huszar, *Intern. Rev. Immunol.* 13:65-93 (1995). Alternatively, the human antibody may be prepared via immortalization of human B lymphocytes producing an antibody directed against a target antigen (such B lymphocytes may be recovered from an individual or may have been immunized in vitro); see, e.g., Cole et al., *Monoclonal Antibodies and Cancer Therapy*, Alan R. Liss, p. 77 (1985); Boerner et al., *J. Immunol.*, 147 (1):86-95 (1991); U.S. Pat. No. 5,750,373.

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementarity determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDRs correspond to those of a non-human immunoglobulin and all or substantially all of the FRs are those of a human immunoglobulin sequence. The humanized antibody optimally also will comprise at least a portion of an immunoglobulin constant region (Fc), typically that of a human immunoglobulin. For further details, see Jones et al., *Nature*, 321:522-525 (1986); Reichmann et al., *Nature*, 332:323-329 (1988); and Presta, *Curr. Op. Struct. Biol.*, 2:593-596 (1992). The humanized antibody includes a PRIMATIZED™ antibody wherein the antigen-binding region of the antibody is derived from an antibody produced by immunizing macaque monkeys with the antigen of interest.

"Single chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the scFv to form the desired structure for antigen binding. For a review of scFv see Plückthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

An "affinity matured" antibody is one with one or more alterations in one or more CDRs thereof which result an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Rio/Technology* 10:779-783 (1992) describes affinity maturation by $V_H$ and $V_L$ domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

An antibody which is "directed against" or which "specifically binds to" an antigen of interest, e.g. DAF antigen, is one capable of binding that antigen with sufficient affinity such that the antibody is useful as a therapeutic agent in targeting the antigen. The antigen here is normally DAF as it exists in a patient to be treated with the antibody (especially the antigen expressed by tumor cells in the patient). Notwithstanding this, various forms of DAF (e.g. native, recombinant, and synthetic DAF, including DAF variants and fragments) may be used to generate or raise the antibody.

The "binding affinity" of an antibody for a target antigen, such as DAF, may be determined by equilibrium methods (e.g. enzyme-linked immunoabsorbent assay (ELISA) or radioimmunoassay (RIA)), or kinetics (e.g. BIACORE™ analysis; see Example 1 below), for example.

To determine whether an antibody binds to an "epitope" on an antigen, such as DAF, bound by another antibody, a routine cross-blocking assay such as that described in *Antibodies, A Laboratory Manual,* Cold Spring Harbor Laboratory, Ed Harlow and David Lane (1988), can be performed.

The term "antibody phage" refers to a bacteriophage with an antibody (particularly an antibody fragment such as a scFv, diabody, linear antibody or Fab) displayed on the surface thereof.

A "naïve antibody phage library" comprises a plurality of antibody phages which have not been derived from an immunized host, i.e. a "non-immunized" phage display library (see, e.g. Vaughan et al. *Nat. Biotechnol.* 14: 309-314 (1996); and Sheets et al. *PNAS (USA)* 95:6157-6162 (1988)). Exemplary methods for generating such "naïve" or "non-immunized" phage libraries are elaborated herein.

The act of "binding" antibody phage to a cell or cell population entails exposing or contacting the antibody phage to/with the cell or cell population under appropriate conditions and for a sufficient period of time such that the antibody displayed on the surface of the phage noncovalently binds to one or more antigens on the cell or cell population. Generally, those antigen(s) to which the antibody bind(s) are present at the surface of a cell (i.e. are "cell surface antigen(s)"). The "antigen" is generally a protein, but may be a non-protein molecule such as a lipid, carbohydrate, glycolipid, nucleic acid etc.

A "live" cell is one which has not been histologically fixed with a fixative such as glutaraldehyde. The live cell may be a "primary" cell which has, e.g., been surgically removed from a mammal or a "cell line" capable of being continuously cultivated in cell culture. A "live cancer cell" is a cancer or tumor cell which has not been histologically fixed and a "live non-cancer cell" is a noncancerous cell (i.e. one which has not been derived from a cancer or tumor) which has not been histologically fixed.

A "distinct" cell or cell population is one which is genotypically and/or phenotypically different from another cell or cell population to which it is being compared. The "distinct" cells or cell populations may however, be of the same tissue-type; for example, a cancer cell and a non-cancer cell of the same tissue type. In the Example below, lung cancer cell lines (1264, SKLU1, A549 and CALU6) and non-cancer lung cell lines (BEAS-2B, CCD19LU and NHBE 4683) were utilized as distinct cell populations.

By "selecting" an antibody phage or antibody is meant choosing for further analysis, or for employment in further method(s), an antibody phage or antibody derived therefrom.

An antibody phage or antibody which "binds selectively" to a cell or cell population is one which binds preferentially to that cell or cell population compared to a distinct cell or cell population. The antibody phage or antibody preferably binds selectively to a cancer cell compared to a non-cancer cell of the same tissue-type. Such selective binding can be determined by a number of methods known in the art including ELISA (with scFv, Fab or antibody phage); flow cytometry (with scFv, Fab or antibody phage); and immunohistochemistry (with scFv, Fab or antibody phage).

The act of "counter-selecting" herein refers to binding antibody phage from an antibody phage library to a first cell or first cell population (e.g. a non-cancer cell or cell population) which is distinct from a second cell or second cell population of interest (e.g. a cancer cell or cancer cell population) and substracting or removing those antibody phage which bind to the first cell or cell population (e.g. the antibody phage which bind to the first cell or first cell population are not subjected to subsequent analyses or screening(s)). This may, for example, be achieved by centrifuging antibody phage bound to the first cell(s) and using the supernatant thereby obtained for further analysis or screening.

"Expression cloning" refers to the act of characterizing a nucleic acid encoding a protein (e.g. a protein antigen) of interest, wherein the method involves detecting that protein expressed by the nucleic acid. Detection is possible using an antibody directed against the protein, e.g., an antibody phage or antibody derived from a naïve phage library as described herein.

"Treatment" refers to both therapeutic treatment and prophylactic or preventative measures. Those in need of treatment include those already with the disorder as well as those in which the disorder is to be prevented. The patient to be treated herein may have, or be predisposed to, cancer (e.g. lung cancer). The patient who is "predisposed" to cancer, may display risk factor(s), such as DAF overexpression and/or expression of a DAF glycoform thought to be associated with cancer.

"Mammal" for purposes of treatment refers to any animal classified as a mammal, including humans, domestic and farm animals, and zoo, sports, or pet animals, such as dogs, horses, cats, cows, etc. Preferably, the mammal is human.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth;

and/or relieve to some extent one or more of the symptoms associated with the disorder. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR).

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, liver cancer, prostate cancer, vulval cancer, thyroid cancer, hepatic carcinoma and various types of head and neck cancer.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nirnustine, ranimustine; antibiotics such as the enediyne antibiotics (e.g. calicheamicin, especially calicheamicin $\gamma_1^I$ and calicheamicin $\theta_1^I$, see, e.g., Agnew Chem Intl. Ed. Engl. 33:183-186 (1994); dynemicin, including dynemicin A; an esperamicin; as well as neocarzinostatin chromophore and related chromoprotein enediyne antiobiotic chromomophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimeterxate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofiran; spirogermanium; tenuazonic acid; triaziquone; 2, 2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhône-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-alpha; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta and -gamma colony stimulating factors (CSFs) such as macrophage-CSF (M-CSF); granulocyte-macrophage-CSF (GM-CSF); and granulocyte- CSF (G-CSF); interleukins (ILs) such as IL-1, IL-1alpha, IL-2, IL-3, IL-4, IL-5, IL-6, IL-7, IL-8, IL-9, IL-10, IL-11, IL-12; a tumor necrosis factor such as TNF-alpha or TNF-beta; and other polypeptide factors including LIF and kit ligand (KL). As used herein, the term cytokine includes proteins from natural sources or from recombinant cell culture and biologically active equivalents of the native sequence cytokines.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society Transactions*, 14, pp. 375-382, 615th Meeting Belfast (1986) and Stella et al., "Prodrugs: A Chemical Approach to Targeted Drug Delivery," *Directed Drug Delivery*, Borchardt et al, (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

The term "package insert" is used to refer to instructions customarily included in commercial packages of therapeutic products, that contain information about the indications, usage, dosage, administration, contraindications and/or warnings concerning the use of such therapeutic products.

Drug combinations that are "synergistic" are those in which the combined action (e.g. the ability to treat cancer) of the drugs is clinically superior to that of each acting separately.

"Decay Accelerating Factor (DAF)" and "CD55" are used interchangeably herein and refer to DAF protein as disclosed in U.S. Pat. No. 5,763,224 and expressly incorporated herein by reference, including variants and isoforms thereof (see U.S. Pat. No. 5,763,224; Caras et al. *Nature* 325: 545-549 (1987); Lublin et al. *J. Immunol.* 137:1629-1635 (1986); Hara et al. *Immunol. Lett.* 37:145-152 (1993); and WO99/43800). Preferred DAF is native sequence human DAF, including native sequence human secreted DAF (DAF-A) and membrane-bound DAF (DAF-B) (Caras et al. *Nature* 325: 545-549 (1987)). This definition specifically includes glycosylation variants of DAF, particularly where those variants are preferentially expressed by tumor cells (such as gastric tumor cells, Hensel et al. *Cancer Research* 59:5399-5306 (1999), or lung tumor cells) compared to normal cells of the same tissue type. An example of a glycosylation variant is the "791Tgp72 antigen" described in WO99/43800, expressly incorporated herein by reference.

Examples of antibodies directed against DAF (or antibodies which specifically bind to DAF) include the murine monoclonal antibodies IA10, IIH6 and VIIIA7 as described in WO86/07062 published Dec. 4, 1986 and expressly incorporated herein by reference; the human antibodies herein designated LU30, LU13 and LU20; the murine 110 and BRIC 216 monoclonal antibodies directed against DAF as described in WO99/43800; the murine 791T36 antibody directed against the 791Tgp72 antigen (ATCC HB9173; WO99/43800); the D17 murine antibody described in Hara et al. *Immunol. Lett.* 37:145-152 (1993) which binds DAF on blood cells, but not in semen or on testis; the human SC-1 antibody (Vollmers et al. *Cancer* 76(4): 550-558 (1995); Vollmers et al. *Cancer Research* 49: 2471-2476 (1989); Vollmers et al. *Oncology Reports* 5:549-522 (1998); and Hensel et al. *Cancer Research* 59:5299-5306 (1999)), as well as variants of any one of the above antibodies. Antibody variants including amino acid sequence variants (e.g. affinity matured antibodies and humanized variants of murine antibodies), glycosylation variants with altered effector function, etc.

A "native sequence" protein comprises the amino acid sequence of a protein as found in nature, e.g. in a human. The native sequence protein can be made by recombinant or other synthetic means, or may be isolated from a native source.

"Percent (%) amino acid sequence identity" herein is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2. The ALIGN-2 sequence comparison computer program was authored by Genentech, Inc. has been filed with user documentation in the U.S. Copyright Office, Washington D.C., 20559, where it is registered under U.S. Copyright Registration No. TXU510087, and is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

II. Modes for Carrying out the Invention

The present application provides a method for making an antibody useful, for example, for cancer diagnosis or therapy, and a method for identifying an antigen which is differentially expressed on the surface of two or more distinct cell populations. These methods employ a naïve antibody phage library that can be prepared according to known techniques, including those discussed below.

Antibody Phage Library Preparation

The antigen-binding domain of an antibody is formed from two variable (V) regions of about 110 amino acids, one each from the light (VL) and heavy (VH) chains, that both present three hypervariable regions. Variable domains can be displayed functionally on phage, for example as single-chain Fv (scFv) fragments, in which VH and VL are covalently linked through a short, flexible peptide, or as Fab fragments, in which they are each fused to a constant domain and interact non-covalently, as described in Winter et al., *Ann. Rev. Immunol.*, 12: 433-455 (1994).

The naïve repertoire of an animal (the repertoire before antigen challenge) provides it with antibodies that can bind with moderate affinity (Kd of about $10^6$ to $10^7$ $M^{-1}$) to essentially any non-self molecule. The sequence diversity of antibody binding sites is not encoded directly in the germline but is assembled in a combinatorial manner from V gene segments. Each combinatorial rearrangement of V-gene segments in stem cells gives rise to a B cell that expresses a single VH-VL combination. Immunization triggers any B cells making a combination that binds the immunogen to proliferate (clonal expansion) and to secrete the corresponding antibody. These naïve antibodies are then matured to high affinity (Kd better than $10^9$ $M^{-1}$) by a process of mutagenesis and selection known as affinity maturation. It is after this point that cells are normally removed to prepare hybridomas and generate high-affinity monoclonal antibodies.

At three stages of this process, repertoires of VH and VL genes can be separately cloned by polymerase chain reaction (PCR) and recombined randomly in phage libraries, which can then be searched for antigen-binding clones as described in Winter et al., *Ann. Rev. Immunol.*, 12: 433-455 (1994). Unlike libraries from immunized sources, a naïve repertoire can be cloned to provide a single source of human antibodies to a wide range of non-self and also self antigens without any immunization as described by Vaughan et al. *Nat. Biotechnol.* 14: 309-314 (1996); and Sheets et al. *PNAS (USA)* 95:6157-6162 (1988). Finally, naïve libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, *J. Mol. Biol.*, 227: 381-388 (1992); and Griffiths et al., *EMBO J.*, 13:3245-3260 (1994).

Phage display mimics the B cell. Filamentous phage is used to display antibody fragments by fusion to the minor coat protein pIII. The antibody fragments can for example be displayed as single chain Fv fragments, in which VH and VL domains are connected on the same polypeptide chain by a flexible polypeptide spacer, e.g. as described by Marks et al., *J. Mol. Biol.*, 222: 581-597 (1991), or as Fab fragments, in which one chain is fused to pIII and the other is secreted into the bacterial host cell periplasm where assembly of a Fab-coat protein structure which becomes displayed on the phage surface by displacing some of the wild type coat proteins, e.g. as described in Hoogenboom et al., *Nucl. Acids Res.*, 19: 4133-4137 (1991). When antibody fragments are fused to the N-terminus of pIII, the phage is infective. However, if the N-terminal domain of pIII is excised and fusions made to the second domain, the phage is not infective, and wild type pIII must be provided by helper phage.

The pIII fusion and other proteins of the phage can be encoded entirely within the same phage replicon, or on different replicons. When two replicons are used, the pIII fusion is encoded on a phagemid, a plasmid containing a phage origin of replication. Phagemids can be packaged into phage particles by "rescue" with a helper phage such as M13K07 that provides all the phage proteins, including pIII, but due to a defective origin is itself poorly packaged in competitions with the phagemids as described in Vieira and Messing, *Meth. Enzymol.*, 153: 3-11 (1987). In a preferred method, the phage display system is designed such that the recombinant phage can be grown in host cells under conditions permitting no more than a minor amount of phage particles to display more than one copy of the Fv-coat protein fusion on the surface of the particle as described in Bass et al., *Proteins*, 8: 309-314 (1990) and in WO 92/09690, published Jun. 11, 1992.

In general, nucleic acids encoding antibody gene fragments are obtained from immune cells harvested from humans or animals. The use of spleen cells and/or B cells or other PBLs from an unimmunized donor provides a better representation of the possible antibody repertoire, and also permits the construction of an antibody library using any animal (human or non-human) species. For libraries incorporating in vitro antibody gene construction, stem cells are harvested from the subject to provide nucleic acids encoding unrearranged antibody gene segments. The immune cells of interest can be obtained from a variety of animal species, such as human, mouse, rat, lagomorpha, luprine, canine, feline, porcine, bovine, equine, and avian species, etc.

Nucleic acid encoding antibody variable gene segments (including VH and VL segments) are recovered from the cells of interest and amplified. In the case of rearranged VH and VL gene libraries, the desired DNA can be obtained by isolating genomic DNA or mRNA from lymphocytes followed by polymerase chain reaction (PCR) with primers matching the 5' and 3' ends of rearranged VH and VL genes as described in Orlandi et al., *Proc. Natl. Acad. Sci. (USA)*, 86: 3833-3837 (1989), thereby making diverse V gene repertoires for expression. The V genes can be amplified from cDNA and genomic DNA, with back primers at the 5' end of the exon encoding the mature V-domain and forward primers based within the J-segment as described in Orlandi et al., supra and in Ward et al, *Nature*, 341: 544-546 (1989). However, for amplifying from cDNA, back primers can also be based in the leader exon as described in Jones et al., *Biotechnol.*, 9: 88-89 (1991), and forward primers within the constant region as described in Sastry et al., *Proc. Natl. Acad. Sci. (USA)*, 86: 5728-5732 (1989). To maximize complementarity, degeneracy can be incorporated in the primers as described in Orlandi et al., supra or Sastry et al., supra. Preferably, the library diversity is maximized by using PCR primers targeted to each V-gene family in order to amplify all available VH and VL arrangements present in the immune cell nucleic acid sample, e.g. as described in the method of Marks et al., *J. Mol. Biol.*, 222: 581-597 (1991) or as described in the method of Orum et al., *Nucleic Acids Res.*, 21: 4491-4498 (1993). For cloning of the amplified DNA into expression vectors, rare restriction sites can be introduced within the PCR primer as a tag at one end as described in Orlandi et al., supra, or by further PCR amplification with a tagged primer as described in Clackson et al., *Nature*, 352: 624-628 (1991).

Repertoires of synthetically rearranged V genes can be derived in vitro from V gene segments. Most of the human VH-gene segments have been cloned and sequenced (reported in Tomlinson et al., *J. Mol. Biol.*, 227: 776-798 (1992)), and mapped (reported in Matsuda et al., *Nature Genet.*, 3: 88-94 (1993); these cloned segments (including all the major comformations of the H1 and H2 loop) can be used to generate diverse VH gene repertoires with PCR primers encoding H3 loops of diverse sequence and length as described in Hoogenboom and Winter, *J. Mol. Biol.*, 227: 381-388 (1992). VH repertoires can also be made with all the sequence diversity focussed in a long H3 loop of a single length as described in Barbas et al., *Proc. Natl. Acad. Sci. USA*, 89: 4457-4461 (1992). One can also make synthetic light chain repertoires (Williams and Winter, *Eur. J. Immunol.*, 23: 1456-1461 (1993)). Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, *J. Mol. Biol.*, 227: 381-388 (1992).

Repertoires of antibody fragments can be constructed by combining VH and VL gene repertoires together in several ways. Each repertoire can be created in different vectors, and the vectors recombined in vitro, e.g., as described in Hogrefe et al., *Gene*, 128: 119-126 (1993), or in vivo by combinatorial infection, e.g., the loxP system described in Waterhouse et al., *Nucl. Acids Res.*, 21: 2265-2266 (1993); and Griffiths et al., *EMBO J.*, 13:3245-3260 (1994). The in vivo recombination approach exploits the two-chain nature of Fab fragments to overcome the limit on library size imposed by *E. coli* transformation efficiency. Naïve VH and VL repertoires are cloned separately, one into a phagemid and the other into a phage vector. The two libraries are then combined by phage infection of phagemid-containing bacteria so that each cell contains a different combination and the library size is limited only by the number of cells present (about $10^{12}$ clones). Both vectors contain in vivo recombination signals so that the VH and VL genes are recombined onto a single replicon and are co-packaged into phage virions. These huge libraries provide large numbers of diverse antibodies of good affinity (Kd of about $10^{-8}$ M).

Alternatively, the repertoires may be cloned sequentially into the same vector, e.g. as described in Barbas et al., *Proc. Natl. Acad. Sci. USA*, 88: 7978-7982 (1991), or assembled together by PCR and then cloned, e.g. as described in Clackson et al., *Nature*, 352: 624-628 (1991). PCR assembly can also be used to join VH and VL DNAs with DNA encoding a flexible peptide spacer to form single chain Fv (scFv) repertoires. In yet another technique, "in cell PCR assembly" is used to combine VH and VL genes within lymphocytes by PCR and then clone repertoires of linked genes as described in Embleton et al., *Nucl. Acids Res.*, 20: 3831-3837 (1992).

The antibodies produced by naïve libraries (either natural or synthetic) can be of moderate affinity (Kd of about $10^6$ to $10^7$ $M^{-1}$), but affinity maturation can also be mimicked in vitro by constructing and reselecting from secondary libraries as described in Winter et al. (1994), supra. For example, mutation can be introduced at random in vitro by using error-prone polymerase (reported in Leung et al., *Technique*, 1: 11-15 (1989)) in the method of Hawkins et al., *J. Mol. Biol.*, 226: 889-896 (1992) or in the method of Gram et al., *Proc Natl. Acad. Sci USA*, 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 96/07754 (published Mar. 14, 1996) describes a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., *Biotechnol.*, 10: 779-783 (1992). This technique allows the production of antibodies and antibody fragments with affinities in the $10^{-9}$ M range.

The antibody phage library of particular interest herein is one which comprises from about $10^9$ to about $10^{15}$ antibody phage.

Screening for Useful Antibodies/Antigens

The naïve antibody phage library is panned with or screened against live cancer cells. The cancer cells may, for example, be surgically removed from a cancer patient or may be derived from a cancer cell line. Various cancer cell lines are publicly available, e.g. from the American Type Culture Collection (ATCC). Exemplary cancer cell lines include breast cancer cell lines such as SK-BR-3, BT-483, MCF-7, BT-20, ZR-751, MDA-MB-231, CAMA1, BT-474; lung adenocarcinoma cell lines such as SKLU1, A549, and 1264; glioma cancer cell lines such as Hs683; ovarian carcinoma lines such as SK-OV-3 and Hey; colorectal carcinoma cell lines including HT-29 and Ls180; prostate carcinoma cell lines such as DU145; gastric carcinoma cell lines exemplified by MS; and renal carcinoma cell lines such as Caki-1. The cancer from which the cancer cell is derived may be a carcinoma, lymphoma, blastoma, sarcoma, or leukemia. Exemplary cancer types from which the cancer cell may be procured include lung cancer, gastrointestinal cancer, pancreatic cancer, glioblastoma, cervical cancer, ovarian cancer, liver cancer, bladder cancer, breast cancer, colon cancer, colorectal cancer, salivary gland carcinoma, kidney cancer, liver cancer, prostate cancer, vulval cancer, thyroid cancer, or hepatic carcinoma. Preferably, the cancer cell is a lung cancer cell.

In a preferred embodiment of the invention, the method includes a counter-selection step using a live non-cancer cell which is preferably of the same tissue type as the cancer cell. Counter-selection can be carried out at any time including before, during and after (or combinations thereof) screening the antibody phage library with the live cancer cells. In the preferred embodiment however, counter-selection precedes at least one step involving panning against the live cancer cells of interest. According to this counter-selection step, the "subtracted" antibody phage (e.g. those present in a supernatant) are then exposed to the live cancer cells. It was surprisingly discovered herein that antibodies against an antigen shared by the cancer cell and non-cancer cell could be identified, in spite of this counter-selection step being performed prior to screening the cancer cell of interest. It was anticipated that such a counter-selection step may have depleted the phage library of antibodies capable of binding the shared antigen.

The non-cancer cells may, for example, have been surgically removed from a patient or may be obtained from some other in vivo source of the cells, or may be derived from a non-cancer cell line, such cell lines being publicly available, e.g., from the ATCC.

The cells to be screened will oftentimes be "adherent" to the extent they adhere to the surface of a cell culture plate or other solid phase in which they are cultured. The present application provides an improved method for detaching the cells from the surface to which they are adhered comprising the use of a solution which does not include any protease and preferably comprises EDTA for detaching the cancer cells. This avoids proteolytic degradation of cell surface antigens resulting from the commonly used trypsin release step.

The cancer and non-cancer cells are not fixed prior to exposure to antibody phage in the antibody phage library. Use of such live cells serves to preserve surface antigens in their native state. Hence, the antibodies prepared according to the present method are more likely to bind the antigen in its endogenous state in a mammal and hence serve as superior diagnostic (e.g. in vivo diagnostic) and therapeutic antibodies.

Antibody phage from the naïve antibody phage library are contacted with, or bound to, the cancer cells (and optionally the non-cancer cells). Prior to this binding step, an aliquot of antibody phage may be blocked to reduce non-specific binding to cell surfaces. Such blocked antibody phage may be added to the cells. Alternatively, the cells, which are optionally blocked, may be added to the antibody phage. The cells and antibody phage are contacted for a sufficient period of time and under suitable conditions such that binding of the phage to cell surface antigen(s) occurs. Such conditions can be determined without undue experimentation. Moreover, panning steps may be repeated as desired to achieve the desired binding between cell surface antigens and antibody phage. Cells may be pelleted in-between panning steps via centrifugation or other means as desired.

Binding of antibody phage or antibody derived from the phage to cells may, for example, be determined by established methodologies such as ELISA, flow cytometry and immunohistochemistry.

Hence, an antibody phage or antibody is selected which binds selectively to the cancer cell of interest Such "cancer-selective" antibodies may be subjected to one or more further analyses. For example, clone analysis (e.g. restriction enzyme cleaving and finger printing and/or DNA sequencing) may be carried out according to known procedures. Alternatively, or additionally, cancer-selectivity of selected antibodies or antibody phage may be determined by comparing binding of the antibodies or antibody phage to cancer cells and non-cancer cells, e.g. of the same tissue type. Such screening may be performed using the cancer and non-cancer cells used to screen the phage library, or other cancer and non-cancer cells.

The selected antibody or antibodies may be altered or modified as desired to generate an antibody particularly adapted for in vivo therapy or diagnosis. Such alteration may involve one or more amino acid substitutions in one or more hypervariable regions of the antibody to increase its affinity for antigen; i.e. the selected antibody may be "affinity matured". Moreover, the antibody or affinity matured antibody may be fused to, or conjugated with, a cytotoxic agent, enzyme (e.g. for ADEPT, see below), detectable label, or other antibody (to generate a bispecific antibody). Such alterations are discussed in more detail below in the Section entitled "Other Methods for Making Antibodies". The variable domain sequences of the antibody or affinity matured antibody may be fused to human constant region sequences so as to generate a larger antibody molecule, such as a Fab, F(ab')$_2$ or intact antibody, depending, for example, on the intended use of the antibody.

Nucleic acid encoding the antibody (which has optionally been altered as explained in the previous paragraph) may be isolated and inserted into a recombinant expression vector and used to transform a suitable host cell for expression of the antibody. Exemplary host cells include prokaryotic host cells (e.g. *E. coli*), yeast cells (such as *Saccharomyces cerevisiae* and *Pichia pastoris*), mammalian cells such as lymphoid cells and Chinese Hamster Ovary (CHO) cells, or plant cells. The expressed antibody recovered from the host cell, may be used for various diagnostic and therapeutic applications such as those discussed hereinbelow.

The present method facilitates identification of an antigen expressed at higher levels on a first cell population (generally a cancer cell) compared to a second cell population (e.g. a non-cancer cell of the same tissue type as the first cell). For example, the level of expression of the antigen on the first cell population or cancer cell may be about two fold or about five fold to about 100 fold or about 1000 fold greater than the level of expression of the antigen on the second cell population or non-cancer cell. Such antigens can be targeted in therapy or diagnosis using antagonists, such as antibodies, or small molecule drugs directed thereagainst. Antibodies directed against such "over-expressed" antigens can be prepared by screening antibody phage libraries as discussed above, or according to other methods for making antibodies available in the art, including those discussed below.

Another advantage of the present invention is the ability to easily expression clone nucleic acid encoding the antigen. To expression clone the antigen, a cDNA library may be prepared, e.g., from the cancer cell used to screen the phage library. The cDNA's thus prepared are expressed in a suitable host cell and expression of the desired protein can be screened for using one or more antibodies selected from the phage library. This way, cDNA encoding the antigen can be identified and sequenced.

In the present Example, an anti-penta-histidine antibody was used to cross-link, via their penta-histidine epitope tags, scFv fragments used to screen for expression of desired antigen. This cross-linking increased the avidity of the interaction between the scFv and antigen. In addition, an anti-mouse antibody was coated on an assay plate and bound the antibody-linked cells to the assay plate.

Other Methods for Making Antibodies

As disclosed above, the present methods provide means for identifying antigens expressed at higher levels on one cell compared to another. Such cells may, for example, be cancer cells and the antigen of interest thereon may be one which is useful for targeting with an antibody for therapy or diagnosis.

Once an antigen is identified as described herein, one can generate further antibodies thereagainst by screening antibody phage libraries as discussed above, or an antibody can be made by other techniques such as those disclosed below.

In one embodiment, a polyclonal antibody is raised against the antigen of interest. Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp.59-103 Academic Press (1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine pliosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp.51-63 Marcel Dekker, Inc., New York, (1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp.59-103 Academic Press (1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.*, 130:151-188 (1992).

The DNA also may be modified, for example, by substituting the coding sequence for human heavy- and light-chain constant domains in place of the homologous murine sequences (U.S. Pat. No. 4,816,567; Morrison, et al., *Proc. Natl Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Methods for humanizing non-human antibodies are well known in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al., *J. Immunol.*, 151:2296 (1993); Chothia et al., *J. Mol. Biol.*, 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., Nature, 362:255-258 (1993); Bruggermann et al., *Year in Immuno.*, 7:33 (1993). Human antibodies can also be derived from phage-display libraries (Hoogenboom et al., *J. Mol. Biol.*, 227:381 (1991); Marks et al., *J. Mol. Biol.*, 222:581-597 (1991)).

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992) and Brennan et al., Science, 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form $F(ab')_2$ fragments (Carter et al., *Bio/Technology* 10:163-167 (1992)). According to another approach, $F(ab')_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185.

Bispecific antibodies are antibodies that have binding specificities for at least two different epitopes. Exemplary bispecific antibodies may bind to two different epitopes of the antigen of interest. Alternatively, an arm which binds antigen of interest may be combined with an arm which binds to a triggering molecule on a leukocyte such as a T-ell receptor molecule (e.g. CD2 or CD3), or Fc receptors for IgG (FcγR), such as FcγRI (CD64), FcγRII (CD32) and FcγRIII (CD16) so as to focus cellular defense mechanisms to the cell expressing the antigen of interest. Bispecific antibodies may also be used to localize cytotoxic agents to cells which express the antigen. These antibodies possess an antigen-binding arm and an arm which binds the cytotoxic agent (e.g. saporin, anti-interferon-γ, vinca alkaloid, ricin A chain, methotrexate or radioactive isotope hapten). Bispecific antibodies can be prepared as full length antibodies or antibody fragments (e.g. $F(ab')_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Milstein et al., Nature 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in WO96/27011, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a tinker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

It may be desirable to modify the antibody of the invention with respect to effector function, so as to enhance the effectiveness of the antibody in treating cancer, for example. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al. *Anti-Cancer Drug Design* 3:219-230 (1989).

The invention also pertains to immunoconjugates comprising an antibody conjugated to a cytotoxic agent such as a chemotherapeutic agent, toxin (e.g. a small molecule toxin or an enzymatically active toxin of bacterial, fungal, plant or animal origin, including fragments and/or variants thereof), or a radioactive isotope (i.e., a radioconjugate).

Chemotherapeutic agents useful in the generation of such immunoconjugates have been described above.

Conjugates of an antibody and one or more small molecule toxins, such as a calicheamicin, a maytansine (U.S. Pat. No. 5,208,020), a trichothene, and CC 1065 are also contemplated herein.

In one preferred embodiment of the invention, the antibody is conjugated to one or more maytansine molecules (e.g. about 1 to about 10 maytansine molecules per antibody molecule). Maytansine may, for example, be converted to May-SS-Me which may be reduced to May-SH3 and reacted with modified antibody (Chari et al. *Cancer Research* 52: 127-131 (1992)) to generate a maytansinoid-antibody immunoconjugate.

Another immunoconjugate of interest comprises an antibody conjugated to one or more calicheamicin molecules. The calicheamicin family of antibiotics are capable of producing double-stranded DNA breaks at sub-picomolar concentrations. Structural analogues of calicheamicin which may be used include, but are not limited to, $\gamma_1^I$, $\alpha_2^I$, $\alpha_3^I$, N-acetyl-$\gamma_1^I$, PSAG and $\theta^I_1$ (Hinman et al. *Cancer Research* 53: 3336-3342 (1993) and Lode et al. *Cancer Research* 58: 2925-2928 (1998)). See, also, U.S. Pat. Nos. 5,714,586; 5,712,374; 5,264,586; and 5,773,001 expressly incorporated herein by reference.

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g. a ribonuclease or a DNA endonuclease such as a deoxyribonuclease; DNase).

A variety of radioactive isotopes are available for the production of radioconjugated anti-DAF antibodies. Examples include $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu.

Conjugates of the antibody and cytotoxic agent may be made using a variety of bifunctional protein coupling agents such as N-succinimidyl-3-(2-pyridyldithiol) propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disucciimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, dimethyl linker or disulfide-containing linker (Chari et al. *Cancer Research* 52: 127-131 (1992)) may be used.

Alternatively, a fusion protein comprising the antibody and cytotoxic agent may be made, e.g. by recombinant techniques or peptide synthesis.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

The antibodies disclosed herein may also be formulated as immunoliposomes. Liposomes containing the antibody are prepared by methods known in the art, such as described in Epstein et al., *Proc. Natl. Acad. Sci, USA*, 82:3688 (1985); Hwang et al., *Proc. Natl Acad. Sci. USA*, 77:4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. *J. Biol. Chem.* 257: 286-288 (1982) via a disulfide interchange reaction. A chemotherapeutic agent is optionally contained within the liposome. See Gabizon et al. *J. National Cancer Inst.* 81(19)1484 (1989).

The antibodies of the present invention may also be used in Antibody Dependent Enzyme Mediated Prodrug Therapy (ADEPT) by conjugating the antibody to a prodrug-activating enzyme which converts a prodrug (e.g. a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as beta-galactosidase and neuraminidase useful for converting glycosylated prodrugs into free drugs; beta-lactamase useful for converting drugs derivatized with beta-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328: 457-458 (1987)). Antibody-abzyme conjugates can be prepared as described herein for delivery of the abzyme to a tumor cell population.

The enzymes of this invention can be covalently bound to the antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., *Nature,* 312: 604-608 (1984)).

Diagnostic Methods

The antibody may also be useful in diagnostic assays, e.g., for detecting expression of an antigen of interest in specific cells, tissues, or serum.

For diagnostic applications, the antibody typically will be labeled with a detectable moiety. Numerous labels are available which can be generally grouped into the following categories:

(a) Radioisotopes, such as $^{35}S$, $^{14}C$, $^{125}I$, $^{3}H$, and $^{131}I$. The antibody can be labeled with the radioisotope using the techniques described in *Current Protocols in Immunology,* Volumes 1 and 2, Coligen et al., Ed. Wiley-Interscience, New York, N.Y., Pubs. (1991) for example and radioactivity can be measured using scintillation counting.

(b) Fluorescent labels such as rare earth chelates (europium chelates) or fluorescein and its derivatives, rhodamine and its derivatives, dansyl, Lissamine, phycoetythrin and Texas Red are available. The fluorescent labels can be conjugated to the antibody using the techniques disclosed in Current Protocols in Immunology, supra, for example. Fluorescence can be quantified using a fluorimeter.

(c) Various enzyme-substrate labels are available and U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in Methods in Enzym. (ed J. Langone & H. Van Vunakis), Academic press, New York, 73:147-166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB));

(ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-p-D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). Thus, indirect conjugation of the label with the antibody can be achieved.

In another embodiment of the invention, the antibody need not be labeled, and the presence thereof can be detected using a labeled antibody which binds to the antibody.

The antibody of the present invention may be employed in any known assay method, such as competitive binding assays, direct and indirect sandwich assays, and immunoprecipitation assays. Zola, Monoclonal Antibodies: A Manual of Techniques, pp.1̂47-158 (CRC Press, Inc. 1987).

The antibody may also be used for in vivo diagnostic assays. Generally, the antibody is labeled with a radionuclide (such as $^{111}$In, $^{16}$Tc, $^{14}$C, $^{111}$I, $^{125}$I, $^3$H, or $^{35}$S) so that the antigen or cells expressing it can be localized using immunoscintiography.

Pharmaceutical Formulations

Therapeutic formulations of the antibodies used in accordance with the present invention are prepared for storage by mixing an antibody having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Preferred lyophilized antibody formulations are described in WO 97/04801, expressly incorporated herein by reference. Liquid formulations including antibodies, e.g. as described in WO98/56418 expressly incorporated herein by reference, are also contemplated The formulation herein may also contain more than one active compound as necessary for the particular indication being treated, preferably those with complementary activities that do not adversely affect each other. For example, it may be desirable to further provide antibodies which bind to EGFR, ErbB2, ErbB3, ErbB4, or vascular endothelial factor (VEGF) in the one formulation. Alternatively, or in addition, the composition may comprise a cytotoxic agent, cytokine or growth inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

Therapeutic Methods

It is contemplated that, according to the present invention, the antibodies may be used to treat various conditions including benign or malignant tumors (e.g. renal, liver, kidney, bladder, breast, gastric, ovarian, colorectal, prostate, pancreatic, lung, vulval, thyroid, hepatic carcinomas; sarcomas; glioblastomas; and various head and neck tumors); leukemias and lymphoid malignancies; other disorders such as neuronal, glial, astrocytal, hypothalamic and other glandular, macrophagal, epithelial, stromal and blastocoelic disorders; and inflammatory, angiogenic and immunologic disorders.

The invention provides a method for treating lung cancer (including small-cell lung cancer; and non-small cell lung cancer; e.g. large cell lung carcinoma, lung adenocarcinoma and squamous cell lung carcinoma) which comprises administering a therapeutically effective amount of an antibody which is directed against or which specifically binds to DAF, where that antibody is optionally conjugated with, or fused to, a cytotoxic agent. The method may also involve co-administering another agent useful in treating lung cancer, such as one or more chemotherapeutic agents (e.g. navelbine, gemcitabine, a taxoid, carboplatin, cisplatin, etoposide, cyclosphosphamide, mitomycin or vinblastine) and/or an additional antibody (such as an anti-ErbB2 antibody, an anti-angiogenic factor antibody, an anti-mucin antibody, or an antibody directed against a different epitope of DAF, etc) and/or other cytotoxic agent(s) and/or a cytokine. An "angiogenic factor" is a growth factor which stimulates the development of blood vessels. The preferred angiogenic factor herein is vascular endothelial growth factor (VEGF). Such co-administration includes treating with the additional agent(s) before, simultaneously with (e.g. in one or two separate formulations, or by administering the two or more agents to the patient via the same IV line, etc), or following, administration of the anti-DAF antibody.

The antibodies of the invention are administered to a human patient, in accord with known methods, such as intravenous (IV) administration as a bolus or by continuous infusion over a period of time, by intramuscular, intraperitoneal, intracerobrospinal, subcutaneous, intra-articular, intrasynovial, intrathecal, oral, topical, or inhalation routes. Intravenous administration of the antibody is preferred.

The treatment of the present invention may involve the combined administration of an antibody and a chemotherapeutic agent. The combined administration includes coadministration, using separate formulations or a single pharmaceutical formulation, and consecutive administration in either order, wherein preferably there is a time period while both (or all) active agents simultaneously exert their biological activities. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992). The chemotherapeutic agent may precede, or follow administration of the antibody or may be given simultaneously therewith. The antibody may be combined with an anti-estrogen compound such as tamoxifen or an anti-progesterone such as onapristone (see, EP 616 812) in dosages known for such molecules.

It may be desirable to also administer antibodies against other tumor associated antigens, such as antibodies which bind to the EGFR, ErbB2, ErbB3, ErbB4, or vascular endothelial factor (VEGF). Sometimes, it may be beneficial to also administer one or more cytokines to the patient.

The patient may also be subjected to radiation therapy in conjunction with administration of the antibody.

For the prevention or treatment of disease, the appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 μg/kg to 15 mg/kg (e.g. 0.1-20 mg/kg) of antibody is an initial candidate dosage for administration to the patient, whether, for example, by one or more separate administrations, or by continuous infusion. A typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

The invention will be more fully understood by reference to the following examples. They should not, however, be construed as limiting the scope of this invention. All literature and patent citations mentioned herein are expressly incorporated by reference.

EXAMPLE 1

In the present example, a large naïve human single chain (sc) Fv phage library was used to search for tumor-associated antigens by panning with a lung adenocarcinoma cell line, 1264, and counter-selecting with a non-tumor bronchial epithelial cell line, BEAS-2B. After 3 rounds of subtractive panning, 239 out of 673 clones analyzed, bound selectively to 1264 tumor cells in a phage ELISA. Diversity analysis of these tumor-selective clones by BstNI fingerprinting and nucleotide sequencing revealed 14 distinct scFv fragments. Four clones bound selectively to 1264 over BEAS-2B cells when analyzed by a more discriminating flow cytometric assay using scFv. Moreover, these clones showed only limited cross-reactivity to several primary human cell lines. One clone, LU30, also cross-reacted strongly with the lung adenocarcinoma line, A549. The LU30 antigen was identified as decay-accelerating factor (DAF, CD55) by expression cloning from a 1264 cDNA library. The mean number of DAF molecules on the surface of 1264 and BEAS cells used for panning and counter-selection were estimated as 75,000±5,000 and 13,000±10,000, respectively. Thus, phage library panning combined with expression cloning permits identification of antibodies and their cognate antigens for proteins that are differentially expressed on the surface of distinct cell populations.

Materials And Methods

Cell Lines. The lung adenocarcinoma line, 1264, was kindly provided by Dr. A. Gazdar, (Simmons Cancer Center, University of Texas-Southwestern, Dallas, Tex.) and grown in RPMI media supplemented with 10% (v/v) FBS. The lung adenocarcinoma cell lines, SKLU1, A549, and CALU6, were obtained from the ATCC and grown in a 1:1 mixture of RPMI and DMEM media supplemented with 10% (v/v) FBS (RPMI/DMEM/FBS). The BEAS-2B cell line, constructed by SV40 transformation of human bronchial epithelial cells, was obtained from the ATCC, as was CCD 19LU, a fibroblast-like cell line isolated from normal human lung. Both BEAS-2B and CCD19LU cells were cultured in RPMI/DMEM/FBS media. Normal human bronchial epithelial (NHBE 4683) and normal human epidermal keratinocytes (NHEK 4021) are primary cell lines (Clonetics, San Diego, Calif.) that were cultured in the serum-free media, BEGM and KGM (Clonetics), respectively. NHBE 4683 and NHEK 4021 lines were used for subtractive panning or analysis between the third and fourth passage. All cell lines were adherent and detached with 2.5 mM EDTA in PBS prior to use.

Live Cell Panning with scFv Phage. An aliquot containing $2.5 \times 10^{12}$ cfu phage, from a large human scFv phage library (Vaughan et al. *Nat. Biotechnol.* 14: 309-314 (1996)) was blocked with 500 µl RPMI containing 10% (v/v) FBS, 1 mM PMSF and 2.5 mM EDTA to reduce non-specific binding to cell surfaces. The blocked phage were added to $1 \times 10^6$ BEAS-2B cells in 500 µl RPMI/DMEM/FBS media and mixed gently for 30 min at ~20° C. Cells were then pelleted, at this and subsequent panning steps, by centrifugation at 500×g for 5 min at 4° C. The phage-containing supernatant was used to resuspend a fresh pellet of $1 \times 10^6$ BEAS-2B cells and incubated for 30 min at ~20° C. followed by pelleting the cells. After repeating this counter-selection step the resultant "subtracted" phage supernatant was incubated with $5 \times 10^6$ 1264 cells for 1 h at ~20° C. with gentle mixing. The cells were pelleted and washed 3 times with PBS. The cell-bound phage were eluted with 0.5 ml PBS containing 100 mM citric acid, pH 2.2 for 10 min and then neutralized with 0.5 ml 1.0 M Tris-HCl, pH 7.5.

*Escherichia coli* strain TG1 (New England Biolabs, Beverley, Mass.) in mid-logarithimic growth phase ($A_{550}$=0.4-0.8) was infected with the eluted phage and plated on 2YT agar containing 2% (w/v) glucose and 50 µg/ml carbenicillin (2YTGC). The resultant colonies were propagated and used to prepare phage (Marks et al., *J. Mol. Biol.*, 222:581-597 (1991)). An aliquot containing ~$1 \times 10^{12}$ cfu phage was used for a second round of panning consisting of 5 counter-selections using $1 \times 10^6$ BEAS-2B cells followed by selection using $1 \times 10^7$ 1264 cells for ~15 h at 20° C. After 10 washes with PBS, the cell-bound phage were eluted and then neutralized as in the first round of panning. The eluted phage were propagated and a third round of panning was performed using $1.0 \times 10^{12}$ cfu phage and the second round protocol.

Cell ELISA with Phage. The scFv-phage were compared in their binding to live tumor and non-tumor cells by ELISA as a primary screen of their binding specificity. After the third round of panning a culture of TG1 was infected with the eluted phage and plated on 2YTGC. Clones for analysis were transferred into 96 well plates with 100 µl 2YT media containing 2% (w/v) glucose and carbenicillin (100 µg/ml) and grown for ~18 h with agitation at 30° C. 50 µl 50% (v/v) glycerol was added to each well of these master plates prior to storage at −70° C.

Replicas of the master plates were prepared and scFv-phage induced by superinfection with M13KO7 helper phage and overnight incubation at 30° C. (Marks et al., *J Mol. Biol.*, 222: 581-597 (1991). The plates were centrifuged (300×g, 5 min. 4° C.) at this and subsequent cell ELISA steps, to pellet the bacteria and 100 µl scFv-phage containing supernatants were transferred to 96 well plates containing 100 µl 6% (w/v) bovine serum albumin in PBS per well. 100 µl of the blocked scFv-phage supernatants were added to parallel plates containing either $1 \times 10^5$ 1264 or BEAS-2B cells per well (1 h, 4° C., gentle agitation). The plates were centrifuged and supernatants aspirated without disturbing the pellets. The cells were washed twice by resuspension in 200 µl 4% (v/v) FBS in PBS (ELISA buffer) at 4° C. followed by centrifugation. Pellets were then resuspended in 100 µl ELISA buffer containing a 1:5,000 dilution of horse radish peroxidase conjugated to a sheep anti-M13 polyclonal (Amersham Pharmacia Biotech, Piscataway, N.J.) and incubated for 20 min at 4° C. Cells were centrifuged and washed 3 times in ELISA buffer. Cell pellets were resuspended in 100 µl TMB reagents (Kirkegaard and Perry Laboratories, Inc., Gaithersburg, Md.) and developed for 10 min prior to quenching with 100 µl 1 M phosphoric acid. The ELISA plates were read ($A_{450}$-A650) using a SPECTRAMAX™ 340 microtiter plate reader (Molecular Devices, Sunnyvale, Calif.) and data analyzed using a spreadsheet program (Microsoft Excel 5.0a).

Flow Cytometry with Phage and scFv. Culture supernatants containing scFv phage were incubated with cells and washed as described above for the cell ELISA with the following modifications. The anti-M 13 polyclonal antibody was used in unconjugated form. After washing, the cells were incubated for 20 min at 4° C. with an R-phycoerythin-conjugated F(ab')$_2$ fragment from a donkey anti-sheep IgG (Jackson Immunoresearch Laboratories, West Grove, Pa.) diluted 1:200 in ELISA buffer, followed by 3 washes and resuspension in 0.5 ml ELISA buffer. Cells were analyzed using a FACScan flow cytometer (Beckton and Dickinson, Mountain View, Calif.).

For cytometric analysis with scFv fragments, $1 \times 10^5$ cells in ELISA buffer were incubated for 1 h at 4° C. with 3 µg/ml scFv fragment. The cells were washed twice by centrifugation and resuspension in ELISA buffer. Cell pellets were then resuspended in 100 µl ELISA buffer containing 1 pg/ml of the anti-hexahistidine monoclonal antibody, BMG-His1 (Boehringer Mannheim, Indianpolis, Ind.). Cells were washed 3 times in ELISA buffer before resuspension in 100 µl ELISA buffer containing a 1:200 dilution of a F(ab')$_2$ fragment of a goat anti-mouse IgG conjugated with FITC (Jackson Immunoresearch laboratories). After 3 additional washes the cells were analyzed by flow cytometry.

Quantitation of Cell Surface DAF. The mean number of DAF molecules per cell was estimated by flow cytometry using a FITC-labeled antibody in comparison with FITC-conjugated beads using the method of Christensen and Leslie *J. Immunol. Methods,* 132: 211-219 (1990) with the following modifications. 250 µg murine anti-DAF monoclonal antibody, IA10, (Genentech) in 50 mM sodium carbonate, pH 8.5 was incubated with 12 µg N-hydroxysuccinimidyl-fluorescein (Pierce, Rockford, Ill.) for 2 h at 20° C., followed by extensive dialysis against PBS. The molar ratio of FITC to protein was determined from the absorbance at 280 nm and 492 nm (Christensen et al., *J. Immunol. Meth-* ods, 132: 211-219 (1990)). Cells were incubated with varying levels of the FITC-labeled anti-DAF antibody to achieve saturation and then prepared for flow cytometry, as above.

Clone Diversity Analysis. The diversity of antigen-positive clones was analyzed by PCR-amplification of the scFv insert using the primers, fdtetseq and PUC 19 reverse (Nissim et al., *EMBO J.*, 13:692-698 (1994)), digestion with BstNI (Marks et al., *J. Mol. Biol.*, 222: 581-597 (1991)) and analysis by polyacrylamide gel electrophoresis. Comparison of BstNI fingerprints was facilitated by digitization of the gel data using an Alphalmager (Alpha Innotech Corp, San Leandro, Calif.) and analysis using ProRFLP version 2.34 (DNA ProScan, Nashville, Tenn.). Up to 10 clones per BstNI fingerprint were then cycle-sequenced using rhodamine-labeled dideoxy chain terminators (Applied Biosystems, Foster City, Calif.), using M13 reverse (New England Biolabs) and mycseq10 primers (Nissim et al., *EMBO J.*, 13:692-698 (1994)). Samples were analyzed using Applied Biosystems Automated DNA Sequencers (models 373 and 377) and sequence data analyzed using the program Sequencher version 3.1 (Gene Codes Corp., Ann Arbor, Mich.).

scFv Production. Selected scFv clones were transformed into TG1 and cultured for 18 h at 30° C. in 2YT media containing 0.2 mM isopropyl-β-D-galactopyranoside to induce scFv expression Periplasmic extracts were prepared by resuspending a bacterial pellet from a 500 ml culture in 10 ml 50 mM sodium phosphate buffer, pH 8.0 containing 0.5 M NaCl, 25 mM imidazole, 0.2 mg/ml hen egg white lysozyme and 1 mM PMSF. After incubation for 1 h at 4° C. the debris was removed by centrifugation. Supernatants were filtered (0.2 μm) and the His-tagged scFv fragments purified by immobilized metal affinity chromatography using $Ni^{2+}$-nitrilotriacetic acid agarose (Qiagen, Valencia, Calif.). The scFv fragments were eluted with 250 mM imidazole in PBS then dialyzed into PBS, flash frozen and stored at −70° C. Clones LU1, LU4, LU13, LU20, and LU30 were grown to high cell density in the fermentor as previously described (Carter et al., *Bio/Technol.*, 10: 163-167 (1992)). scFv fragments were purified from 2 g fermentation pastes as for cell pellets from shake flasks.

cDNA Library Construction. Total cellular RNA was purified from guanidine thiocyanate homogenates from 6 g of cultured 1264 cells (Chirgwin et al., *Biochemistry*, 18: 5294-5299, (1979)). mRNA was isolated from the total RNA using oligo-d(T) cellulose (Collaborative Research, Bedford, Mass.) (Aviv et al., *Proc. Natl. Acad. Sci. USA*, 69:1408-1412 (1972)). Oriented cDNA transcripts were prepared from 5 pg poly-(A)+ mRNA using the SuperScript Plasmid System (Gibco BRL, Gaithersburg, Md.), fractionated by electrophoresis on a 5% polyacrylamide gel and size selected in the ranges of 0.6-2.0 kb and >2 kb. Eluted cDNAs were ligated into the XhoI and NotI sites of the mammalian expression vector pRK5 (Suva et al., *Science*, 237:893-896 (1987)), and then electroporated into DH10B (Gibco BRL) cells under conditions recommended by the supplier.

Antigen Expression-cloning from cDNA Library. DNA from 10 pools of 50,000 clones each of the 0.6-2 kb and >2 kb cDNA libraries was prepared for expression-cloning the antigens recognized by tumor-selective scFv fragments. 10 μg plasmid DNA from each of the 20 pools was electroporated into $2\times10^6$ COS7 cells in 180 μl PBS using 4 mm gap cuvettes with a Gene Pulser electroporator (BioRad, Hercules, Calif.) with an applied voltage of 300 V and a capacitance of 125 μF. After incubation for 72 h at 37° C. the COS7 cells were detached with 2.5 mM EDTA in PBS. The cells were washed and then incubated in 1 ml growth media containing one or more purified scFv fragment (10 μg/ml each) for 1 h at 4° C. The cells were washed twice to remove unbound scFv, resuspended in 1 ml media containing 5 μg anti-penta-histidine antibody (Qiagen) and incubated for 1 h at 4° C. After 2-3 washes the cells were resuspended in 5 ml media and transferred to a polystyrene dish coated with a polyclonal anti-mouse IgG (ICN/Cappel, Aurora, Ohio) and allowed to bind for 1 h at 4° C. Plates were washed gently 3-4 times with PBS. Remaining attached cells were lysed, plasmid DNA extracted and amplified (Seed et al., *Proc Natl. Acad. Sci. USA*, 84: 3365-3369 (1987)). This DNA was then electroporated into COS7 cells for additional panning. In one case, an increasing number of cells were captured during the second to fourth rounds of panning. Plasmid DNA extracted from the COS7 cells was transformed into TG1 and single colonies were picked into 96 well plates. DNA was prepared from pools of 10-20 clones each, electroporated into COS7 cells and panned with scFv fragments as described above. Pools of clones positive for cells binding to the petri dishes were broken down from the *E. coli* master plates and individual clones tested by panning. An individual positive clone was cycle-sequenced using rhodamine-labeled dideoxy chain terminators.

Affinity Measurements. Kinetic measurements were made by surface plasmon resonance using a BIACORE 1000™ Biosensor (Biacore, AB Uppsala, Sweden). CM-5 chips were functionalized with 350 response units recombinant human DAF in 10 mM sodium acetate (pH 4.6) or 8,000 response units bovine serum albumin as a negative control. The DAF-derivatized chip was saturated with LU30 scFv (25-100 nM) by injecting this fragment at 10 μl/min in PBS containing 0.5% (w/v) bovine serum albumin and 0.05% (v/v) TWEEN 20™. The resultant sensorgrams were analyzed using BIAEVALUATION™ software 3.0.

Results

Subtractive Cellular Panning with scFv Phage. A large human scFv-phage library (Vaughan et al. *Nat. Biotechnol.* 14: 309-314 (1996)) was used to search for novel tumor-associated antigens by panning with the lung adenocarcinoma cell line, 1264, and counter-selecting with the non-tumor bronchial epithelial cell line, BEAS-2B. Precautions were taken to maintain the integrity of membrane antigens during panning to facilitate subsequent identification of antigen by expression-cloning using isolated scFv fragments. Firstly, live rather than fixed cells were used for panning in an attempt to preserve surface antigens in their native state. Secondly, cells grown adherently were detached with EDTA alone, thereby avoiding proteolytic degradation of cell surface antigens resulting from the commonly used trypsin release step.

The number of phage recovered after 1, 2 and 3 rounds of panning was $1.5\times10^7$, $7.0\times10^5$ and $4.0\times10^6$ cfu, respectively. The phage populations after each round of panning were analyzed by flow cytometry. The phage from the third round showed a large increase in binding to 1264 cells and a slightly smaller increase with BEAS-2B cells when compared to phage from prior rounds and unselected phage (FIG. 1). This apparent differential increase in binding to 1264 over BEAS-2B cells encouraged us to screen individual phage from the third round population for selective binding to the 1264 tumor cells.

Analysis of Clone Specificity and Diversity. The binding specificity of individual clones from the third round of panning was analyzed by ELISA using scFv-phage and live cells. The primary criteria used to assess tumor-selectivity were robust binding to 1264 cells (ELISA signal: $A_{450}-A_{650} \geq 0.3$) and much weaker if detectable binding to BEAS-2B cells ($\geq$10-fold lower ELISA signal). The diversity of clones satisfying these primary criteria was assessed by BstNI fingerprinting of the PCR-amplified scFv fragments, and nucleotide sequencing of up to 10 clones per fingerprint pattern. A small number of clones that did not satisfy the primary criteria were also fingerprinted (n=29) and sequenced (n=11). Secondary criteria were then used to chose unique and apparently tumor-selective clones for further analysis: 1) unambiguous fingerprint pattern, 2) open reading frame for scFv, 3) majority of clones which share the same nucleotide sequence also satisfy the primary selection criteria.

Figure 2:
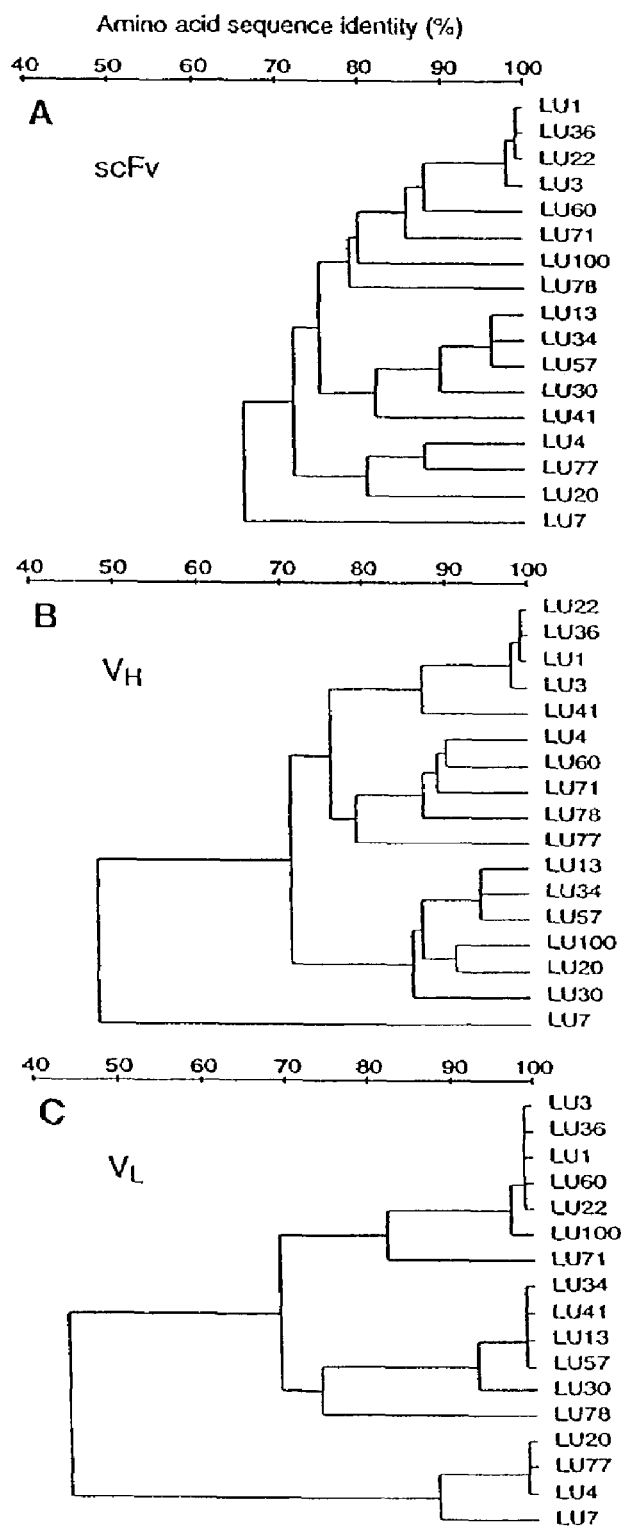
FIGS. 2A-C depict dendrograms for tumor-selective scFv satisfying primary and secondary selection criteria (Table 1). Comparisons were made between scFv amino acid sequences (FIG. 2A) as well as their component $V_H$ domains (FIG. 2B), and $V_L$ domains (FIG. 2C).

Out of 673 clones analyzed, 239 satisfied the primary criteria for selective binding and 197 clones could be assigned to 15 different BstNI fingerprint patterns (Table 1). In the majority of cases (13/15) one fingerprint pattern gave rise to a single nucleotide sequence, whereas in 2/15 cases 2 different sequences were found with indistinguishable BstNI fingerprint patterns. Thus a total of 17 scFv clones were identified that satisfy the secondary selection criteria. The 2 most abundant clones, fingerprints types 1 and 2, represented ~80% of the clones satisfying the secondary criteria. In contrast, the other 15 clones each represent $\geq$5% of the clones identified. Four of the 17 clones (LU1, LU3, LU22 and LU36) are very closely related (>97% amino acid identity for scFv) (FIG. 2A). Thus from the 673 clones initially screened, 14 distinct scFv clones were identified that show selective binding to BEAS-2B cells as judged by phage ELISA. These 14 distinct scFv fragments have divergent $V_H$ sequences (FIG. 2B) whereas their corresponding $V_L$ domains are more limited in diversity (FIG. 2C). Indeed, many of the scFv clones isolated utilize identical or very closely related VL sequences as previously noted (Vaughan et al. *Nat. Biotechnol.* 14: 309-314 (1996); Merchant et al., *Nat. Biotechnol.* 16: 677-681 (1998)). This reflects the very limited size of the light chain repertoire in the phage library.

Figure 3:
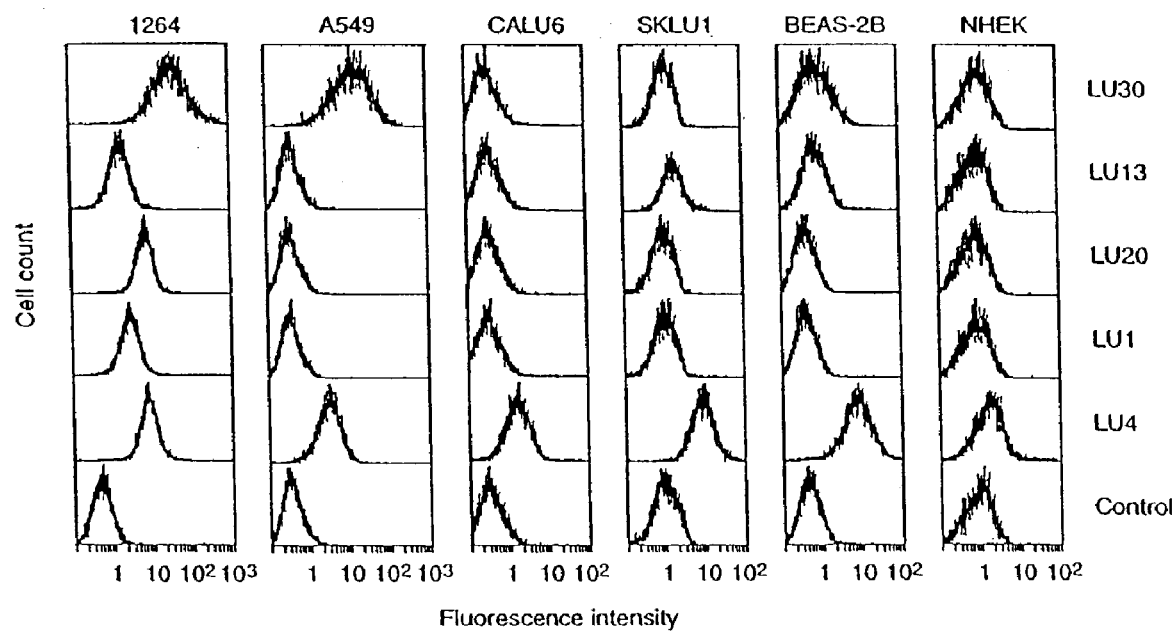
FIG. 3 shows flow cytometric analysis of scFv fragments with tumor (1264, A549, CALU6 and SKLU1) and non-tumor (BEAS-2B and NHEK) cell lines.

Stringent Analysis of Clone Specificity. The 14 distinct clones that satisfied the secondary selection criteria (Table 1) were further analyzed by a more discriminating but low throughput flow cytometric screen using scFv fragments (representative data in FIG. 3). Four clones, namely LU1, LU13, LU20 and LU30, demonstrated significant binding to 1264 cells but minimal cross-reactivity to BEAS-2B cells. In contrast, the remaining clones, (represented by LU4 in FIG. 3) showed significant cross-reactivity to BEAS-2B. Clone LU30, which gave the most pronounced binding to 1264, also gave strong staining of 1/3 additional lung adnenocarcinoma lines tested (A549). Clones LU1, LU13, LU20 and LU30 showed minimal cross-reactivity to BEAS-2B and the primary human line, NHEK 4021 (FIG. 3). Flow cytometric analysis with the primary human lines, CCD-19LU and NHBE 4683, gave very similar binding between LU1, LU13, LU20 and LU30 phage as control phage, albeit with substantially higher background binding than for the other lines.

Figure 4:
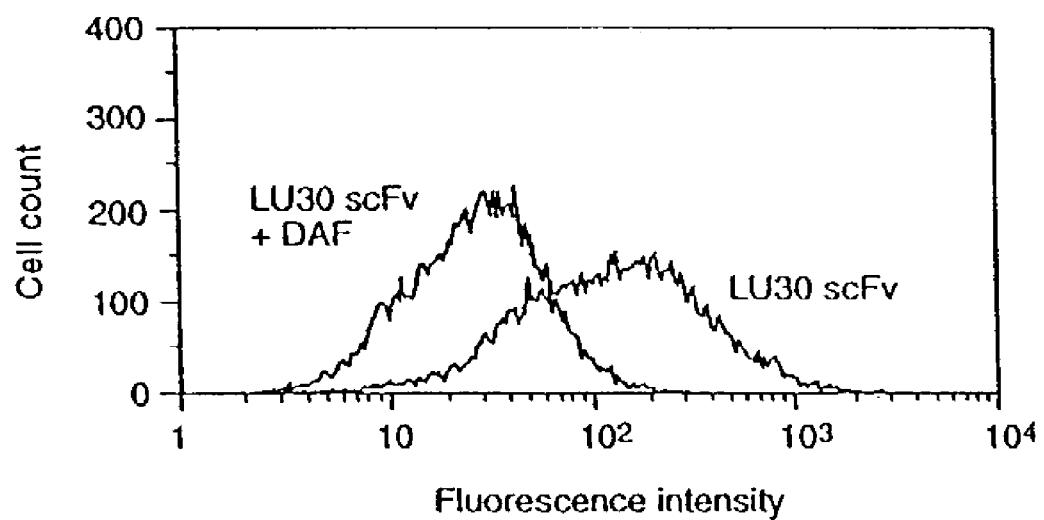
FIG. 4 shows binding of LU30 scFv (3 µg/ml) to 1264 cells in the absence and presence of recombinant human DAF (30 µg/ml).

Expression Cloning of LU30 Antigen. ScFv fragments corresponding to clones LU13, LU20 and LU30 were prepared by secretion from *E. coli* and immobilized metal affinity chromatography and used for expression cloning. Panning was performed using a mixture of these 3 scFv fragments and a cDNA expression library constructed from 1264 cells that was transiently expressed in COS7 cells. After 3 rounds of panning using a mixture of these 3 scFv fragments, efficient cell capture was demonstrated with some plasmid pools using LU30 but not LU13 and LU20 scFv fragments. Repeated panning using clones LU13 and LU20 in the absence of LU30 was also unsuccessful. Positive pools for clone LU30 were broken down first into smaller pools and then into individual clones. This led to the identification of a single clone expressing a protein that bound specifically to the LU30 scFv fragment. Nucleotide sequence analysis of this clone identified it as decay accelerating factor (DAF, CD55). Binding of LU30 scFv (GenBank accession number AF117206) to 1264 cells could be competed with recombinant human DAF (FIG. 4) but not with the anti-DAF monoclonal antibody, IA10 (data not shown). Further confirmation of LU30 binding to DAF was provided by affinity measurements obtained using a BIACORE™ instrument: $K_{d}=(13\pm5)$ nM, $k_{on}=(3.4\pm1.0)\times10^5$ $M^{-1}s^{-1}$, $k_{off}=(4.5\pm1.3)\times10^{-3}s^{-1}$.

Cellular DAF Levels. The mean number of DAF molecules on 1264 and BEAS-2B cell lines was estimated by quantitative flow cytometry using an anti-DAF IgG labeled with a mean number of 5.3 FITC molecules in comparison with standards. The number of DAF molecules on the 1264 tumor cells used for panning and BEAS non-tumor cells used for counter-selection were estimated as 75,000±5,000 and 13,000±10,000, respectively. Attempts to estimate the number of DAF sites on BEAS-2B and 1264 using this methodology with the LU30 scFv fragment were unreliable since FITC labeling of LU30 scFv impaired its binding to DAF.

Discussion

Four scFv fragments were identified that bound more extensively to one or more tumor cell lines than to related non-tumor cell line(s) by subtractive panning of live cells with a large naïve antibody phage library. The cognate antigen corresponding to one scFv clone, LU30, was identified as DAF by expression cloning. DAF is expressed at approximately 6-fold greater levels on 1264 cells than BEAS cells used for counter-selection. Thus the counter-selection process is not 100% efficient, permitting identification of a scFv fragment that binds to antigen that is present at much higher levels on target than control cells. This bodes well for the utility of this method since cell surface antigens that are overexpressed in tumors compared to normal tissues occur frequently, e.g. HER2/neu (Tzahar et al., *Biochim. Biophys. Acta*, 1377:M25-M37 (1998)) and EGFR (Voldborg et al., *Annals Oncol.*, 8:1197-1206 (1997)).

Antibody phage panning method offers a potential direct and broadly applicable route to the identification of human antibodies suitable for anti-tumor therapy. This strategy likely favors the identification of antibodies to highly expressed antigens, such as DAF shown here, since high antigen levels are anticipated to facilitate enrichment of cognate-scFv phage during panning. This seems desirable since high level antigen expression may also facilitate tumor localization of anti-tumor antibodies in vivo.

Antibody phage panning could potentially identify tumor-associated antigens resulting from post-translational modifications that differ between tumor and non-tumor cells, e.g., the mucin product of the MUC1 gene is underglycosylated in many human tumors (Barratt-Boyes et al., *Cancer Immunol. Immunother.*, 43:142-151 (1996)) exposing new epitopes for antibody targeting. This has prompted the development of humanized anti-MUC1 antigen (Couto et al., *Adv. Exp. Med. Biol.*, 353:55-59 (1994); Couto et al., *Hybridoma*, 13:215-219 (1994); Baker et al, *Adv. Exp. Med. Biol.*, 353: 61-82 (1994)). Furthermore human antibodies recognizing MUC1 on tumor cells have been identified by panning with a MUC1 peptide (Henderikx et al., *Cancer Res.* 58: 4324-4332 (1998)). In contrast, such post-translational differences between tumor and non-tumor cells will not be detected by powerful high throughput transcriptome and genomic methods, such as differential display (Liang et al., *Curr. Opin. Immunol.* 7: 274-280 (1995)) cDNA (Schena, M. et al., *Science,* 270:467-470 (1995); DeRisi et al., *Nat. Genet.,* 14:457-460 (1996)) or oligonucleotide (Chee et al. *Science,* 274: 610-614 (1996)) microarray and SAGE (Velculescu et al., *Science,* 276:1268-1272 (1997); Zhang et al. *Science,* 276:1268-1272 (1997);

Hibi et al., *Cancer Res.,* 58: 5690-5694 (1998)). Transcriptome and genomic methods will also fail to detect proteins which are overexpressed in tumors despite unchanged RNA transcript levels and gene copy number, respectively.

SAGE has identified significant differences in RNA transcript levels between primary human tumors and tumor cells lines (Zhang et al. *Science,* 276:1268-1272 (1997)). This raises the possibility that antibody phage panning may detect tumor-associated antigens found on primary human tumors but not cell lines. Conversely antibodies may be identified that are cell line specific as judged by failure to bind primary human tumor cells. Direct panning on primary human tumor cells is anticipated to avoid these problems.

As judged by immunoaffinity purification followed by western blotting with the anti-DAF monoclonal antibody IA10 (WO86/07062), LU20 and LU13 were also found to bind to DAF. The VL and VH sequences of the LU30, LU20 and LU13 antibodies are shown in FIGS. 5A and 5B.

EXAMPLE 2

This Example describes how one may treat a human patient with lung cancer with a human antibody as described herein.

The VH and VL domains of the human antibody LU30 identified as described in the previous Example are joined to human IgG1 constant domains to generate an intact antibody with effector functions in vivo. The antibody may be expressed in a Chinese Hamster Ovary (CHO) cell (U.S. Pat. No. 4,816,567, expressly incorporated herein by reference). The recombinant antibody is recovered from the CHO cells and formulated as a lyophilized preparation which can be reconstituted with bacteriostatic water for injection (BWFI) to generate a reconstituted formulation for intravenous or subcutaneous administration to a human patient (see WO 97/04801). The reconstituted formulation is administered to a human patient diagnosed as having lung cancer, e.g. in an initial loading dose of about 4 mg/kg IV followed by weekly doses of about 2 mg/kg IV. Candidate patients for therapy may optionally be screened to determine whether they express variant DAF (e.g. a glycosylation variant of DAF) which is preferentially expressed on cancerous lung tissue as opposed to normal (i.e. noncancerous) lung tissue and/or to establish whether their tumor overexpresses DAF. Immunohistochemistry and DNA-based assays (e.g. fluorescent in situ hybridization, FISH) that can be used to determine gene amplification and/or protein overexpression are readily available in the art. The human antibody, LU30, may for instance be used to assess DAF overexpression via IHC. The anti-DAF antibody is optionally combined with other cytotoxic agents used to treat lung cancer, such as navelbine, gemcitabine, a taxoid, carboplatin, cisplatin, etoposide, cyclophosphamide, mitomycin, vinblastine and/or an additional antibody (such as an anti-ErbB2 antibody, anti-angiogenic factor antibody, an anti-mucin antibody, or an antibody directed against a different epitope of DAF) in amounts conventially used for such agents. Administration of the anti-DAF antibody to the patient is anticipated to increase the time to disease progression, result in higher overall response rates (ORRs), increase the median duration of response and/or increase 1-year survival rate compared to placebo-treated patients.

What is claimed is:

1. An isolated human antibody directed against human decay accelerating factor (DAF) which has a binding affinity for human DAF of about 10 nM or better, and which binds an epitope on DAF bound by an antibody selected from the group consisting of LU30 having variable light chain and heavy chain sequences of SEQ ID NOs: 1 and 4, respectively, LU13 having variable light chain and heavy chain sequences of SEQ ID NOs: 2 and 5, respectively, and LU20 having variable light chain and heavy chain sequences of SEQ ID NOs: 3 and 6, respectively.

2. The antibody of claim 1 comprising antigen-binding amino acid residues of an antibody selected from the group consisting of LU30 having variable light chain and heavy chain sequences of SEQ ID NOs: 1 and 4, respectively, LU13 having variable light chain and heavy chain sequences of SEQ ID NOs: 2 and 5, respectively, and LU20 having variable light chain and heavy chain sequences of SEQ ID NOs: 3 and 6, respectively.

3. The antibody of claim 1 which is selected from the group consisting of LU30 having variable light chain and heavy chain sequences fo SEQ ID NOs: 1 and 4, respectively, LU13, having variable light chain and heavy chain sequences of SEQ ID NOs: 2 and 5, respectively and LU20, having variable light chain and heavy chain sequences of SEQ ID NOs: 3 and 6, respectively.

4. A pharmaceutical composition comprising the antibody of claim 1 and a pharmaceutically acceptable carrier.

5. An article of manufacture comprising the pharmaceutical composition of claim 4 and a package insert instructing the user of the composition to treat a patient having lung cancer, or predisposed to lung cancer, with said composition, wherein said patient having lung cancer or predisposed to lung cancer exhibits overexpression of Decay Accelerating Factor bound by the antibody of the composition.

6. The article of manufacture of claim 5 wherein the lung cancer is selected from the group eonsisting of small-cell lung cancer, non-small cell lung cancer, large cell lung carcinoma, lung adenocarcinoma, and squamous cell lung carcinoma.

* * * * *

SEQUENCE LISTING

```
<160> NUMBER OF SEQ ID NOS: 6

<210> SEQ ID NO 1
<211> LENGTH: 110
<212> TYPE: PRT
<213> ORGANISM: Homo sapiens

<400> SEQUENCE: 1

Gln Ser Val Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Phe
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Val
65                  70                  75                  80

Gln Ala Glu Asp Glu Ala Asp Tyr Tyr Cys Ser Ser Tyr Thr Ser Ala
                85                  90                  95
```

-continued

Ser Thr Val Ile Phe Gly Gly Gly Thr Lys Leu Thr Val Leu
            100                 105                 110

<210> SEQ ID NO 2
<211> LENGTH: 110
<212> TYPE: PRT
<213> ORGANISM: Homo sapiens

<400> SEQUENCE: 2

Gln Ser Val Leu Thr Gln Pro Ala Ser Val Ser Gly Ser Pro Gly Gln
 1               5                  10                  15

Ser Ile Thr Val Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Gly Ser Lys Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Arg
                85                  90                  95

Ser Thr Arg Val Phe Gly Gly Gly Thr Lys Leu Thr Val Leu
            100                 105                 110

<210> SEQ ID NO 3
<211> LENGTH: 107
<212> TYPE: PRT
<213> ORGANISM: Homo sapiens

<400> SEQUENCE: 3

Asp Ile Gln Met Thr Gln Ser Pro Ser Thr Leu Ser Ala Ser Ile Gly
 1               5                  10                  15

Asp Arg Val Thr Ile Thr Cys Arg Ala Ser Glu Gly Ile Tyr His Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Ala Ser Gly Ala Pro Ser Arg Phe Ser Gly
        50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Tyr Ser Asn Tyr Pro Leu
                85                  90                  95

Thr Phe Gly Gly Gly Thr Lys Leu Glu Ile Lys
            100                 105

<210> SEQ ID NO 4
<211> LENGTH: 121
<212> TYPE: PRT
<213> ORGANISM: Homo sapiens

<400> SEQUENCE: 4

Gln Val Lys Leu Gln Glu Ser Gly Gly Gly Leu Val Gln Pro Gly Gly
 1               5                  10                  15

Ser Leu Lys Leu Ser Cys Ala Ala Ser Gly Phe Thr Phe Ser Gly Tyr
                20                  25                  30

Gly Met Ser Trp Ile Arg Gln Thr Pro Asp Lys Arg Leu Glu Trp Val
            35                  40                  45

```
Ala Thr Ile Asn Ser Gly Gly Ser Tyr Thr Tyr Tyr Ser Asp Ser Val
         50                  55                  60

Lys Gly Arg Phe Thr Ile Ser Arg Asp Asn Val Lys Asn Thr Leu Tyr
 65                  70                  75                  80

Leu Gln Met Ser Ser Leu Lys Ser Glu Asp Thr Ala Met Tyr Tyr Cys
                 85                  90                  95

Ala Arg Arg Asn Gly Thr Leu Tyr Tyr Tyr Leu Met Asp Tyr Trp Gly
                100                 105                 110

Arg Gly Thr Leu Val Thr Val Ser Ser
            115                 120

<210> SEQ ID NO 5
<211> LENGTH: 115
<212> TYPE: PRT
<213> ORGANISM: Homo sapiens

<400> SEQUENCE: 5

Gln Val Gln Leu Gln Glu Ser Gly Gly Asn Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Ala Ile Ser Gly Ser Gly Gly Asn Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Thr Leu Arg Ala Glu Asp Thr Ala Val Tyr Tyr Cys
                 85                  90                  95

Ala Arg Arg Ala Ser Tyr Asp Tyr Trp Gly Gln Gly Thr Met Val Thr
                100                 105                 110

Val Ser Ser
        115

<210> SEQ ID NO 6
<211> LENGTH: 122
<212> TYPE: PRT
<213> ORGANISM: Homo sapiens

<400> SEQUENCE: 6

Glu Val Gln Leu Val Glu Thr Gly Gly Gly Leu Val Gln Pro Gly Arg
  1               5                  10                  15

Ser Leu Arg Leu Ser Cys Ala Ala Ser Gly Phe Thr Phe Glu Asp Tyr
                 20                  25                  30

Gly Met His Trp Val Arg Gln Ala Pro Gly Lys Gly Leu Glu Trp Val
             35                  40                  45

Ser Gly Ile Asn Trp Asn Gly Ser Thr Gly Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Arg Asp Ala Pro Ser Gly Ser Tyr Gly Tyr Trp Phe Asp Pro Trp
                100                 105                 110

Gly Gln Gly Thr Leu Val Thr Val Ser Ser
            115                 120
```